(12) United States Patent
Gutfinger et al.

(10) Patent No.: US 7,794,404 B1
(45) Date of Patent: Sep. 14, 2010

(54) SYSTEM AND METHOD FOR ESTIMATING CARDIAC PRESSURE USING PARAMETERS DERIVED FROM IMPEDANCE SIGNALS DETECTED BY AN IMPLANTABLE MEDICAL DEVICE

(75) Inventors: Dan E. Gutfinger, Irvine, CA (US); Neal L. Eigler, Pacific Palisades, CA (US); Dorin Panescu, San Jose, CA (US); James S. Whiting, Los Angeles, CA (US)

(73) Assignee: Pacesetter, Inc, Sunnyvale, CA (US)

( * ) Notice: Subject to any disclaimer, the term of this patent is extended or adjusted under 35 U.S.C. 154(b) by 629 days.

(21) Appl. No.: 11/559,235

(22) Filed: Nov. 13, 2006

Related U.S. Application Data

(63) Continuation-in-part of application No. 11/558,101, filed on Nov. 9, 2006.

(60) Provisional application No. 60/787,884, filed on Mar. 31, 2006.

(51) Int. Cl.
*A61B 5/02* (2006.01)
(52) U.S. Cl. .......................................... 600/486; 607/23
(58) Field of Classification Search ................ 600/508, 600/517, 485, 486, 506, 513, 526, 547; 607/17, 607/23
See application file for complete search history.

(56) References Cited

U.S. PATENT DOCUMENTS

| | | | |
|---|---|---|---|
| 3,934,458 A | 1/1976 | Beretsky | |
| 4,535,774 A | 8/1985 | Olson | |
| 4,686,987 A | 8/1987 | Salo et al. | |
| 4,873,987 A | 10/1989 | Djordjevich | |
| 5,003,976 A | 4/1991 | Alt | |
| 5,042,303 A | 8/1991 | Geluk | |
| 5,054,485 A | 10/1991 | Cohen | |

(Continued)

FOREIGN PATENT DOCUMENTS

WO    WO 96/15827    5/1996

(Continued)

OTHER PUBLICATIONS

Stutz, Michael. "All about Circuits: Conductance." Copyright 1999-2000. <http://www.allaboutcircuits.com/vol_1/chpt_5/4.html>.*

(Continued)

*Primary Examiner*—Carl H Layno
*Assistant Examiner*—Gary A Porter, Jr.
(74) *Attorney, Agent, or Firm*—Steven M. Mitchell

(57) ABSTRACT

Techniques are provided for estimating left atrial pressure (LAP) or other cardiac pressure parameters based on various parameters derived from impedance signals. In particular, effective LAP is estimated based on one or more of: electrical conductance values, cardiogenic pulse amplitudes, circadian rhythm pulse amplitudes, or signal morphology fractionation values, each derived from the impedance signals detected by the implantable device. Predetermined conversion factors stored within the device are used to convert the various parameters derived from the electrical impedance signal into LAP values or other appropriate cardiac pressure values. The conversion factors may be, for example, slope and baseline values derived during an initial calibration procedure performed by an external system, such as an external programmer. In some examples, the slope and baseline values may be periodically re-calibrated by the implantable device itself.

60 Claims, 22 Drawing Sheets

U.S. PATENT DOCUMENTS

| | | | |
|---|---|---|---|
| 5,105,810 A | 4/1992 | Collins | |
| 5,119,813 A | 6/1992 | Cohen | |
| 5,156,148 A | 10/1992 | Cohen | |
| 5,179,946 A | 1/1993 | Weiss | |
| 5,184,614 A | 2/1993 | Collins | |
| 5,190,035 A | 3/1993 | Salo et al. | |
| 5,201,865 A | 4/1993 | Kuehn | |
| 5,282,840 A | 2/1994 | Hudrlik | |
| 5,300,093 A | 4/1994 | Koestner et al. | |
| 5,305,745 A | 4/1994 | Zacouto | |
| 5,330,505 A | 7/1994 | Cohen | |
| 5,391,190 A | 2/1995 | Pederson | |
| 5,417,717 A | 5/1995 | Salo | |
| 5,476,484 A | 12/1995 | Hedberg | |
| 5,507,785 A | 4/1996 | Deno | |
| 5,531,772 A | 7/1996 | Prutchi | |
| 5,690,611 A | 11/1997 | Swartz | |
| 5,713,935 A | 2/1998 | Prutchi | |
| 5,746,214 A | 5/1998 | Brown | |
| 5,792,194 A | 8/1998 | Morra | |
| 5,800,467 A * | 9/1998 | Park et al. | 607/17 |
| 5,814,088 A | 9/1998 | Paul | |
| 5,954,752 A | 9/1999 | Mongeon | |
| 5,957,861 A | 9/1999 | Combs | |
| 6,198,965 B1 | 3/2001 | Penner | |
| 6,208,900 B1 | 3/2001 | Ecker | |
| 6,219,579 B1 | 4/2001 | Bakels | |
| 6,223,082 B1 | 4/2001 | Bakels | |
| 6,251,303 B1 | 6/2001 | Bawendi | |
| 6,275,727 B1 | 8/2001 | Hopper | |
| 6,278,894 B1 | 8/2001 | Salo et al. | |
| 6,317,626 B1 | 11/2001 | Warman | |
| 6,337,994 B1 | 1/2002 | Stoianovici | |
| 6,459,929 B1 | 10/2002 | Hopper | |
| 6,473,640 B1 | 10/2002 | Eriebacher | |
| 6,473,647 B1 | 10/2002 | Bradley | |
| 6,501,983 B1 * | 12/2002 | Natarajan et al. | 600/517 |
| 6,508,771 B1 | 1/2003 | Padmanabhan | |
| 6,512,949 B1 | 1/2003 | Combs | |
| 6,527,729 B1 | 3/2003 | Turcott | |
| 6,539,261 B2 | 3/2003 | Dal Molin | |
| 6,595,927 B2 | 7/2003 | Pitss-Crick | |
| 6,620,186 B2 | 9/2003 | Saphon | |
| 6,714,811 B1 | 3/2004 | Padmanabhan | |
| 6,754,530 B2 | 6/2004 | Bakels | |
| 6,970,742 B2 | 11/2005 | Mann | |
| 7,027,866 B2 | 4/2006 | Warkentin | |
| 7,065,400 B2 | 6/2006 | Schechter | |
| 7,065,403 B1 | 6/2006 | Mouchawar | |
| 7,127,290 B2 | 10/2006 | Girouard | |
| 7,139,609 B1 | 11/2006 | Min | |
| 7,139,610 B2 | 11/2006 | Ferek-Petric | |
| 7,181,283 B2 | 2/2007 | Hettrick | |
| 7,184,821 B2 | 2/2007 | Belalcazar | |
| 7,200,442 B1 | 4/2007 | Koh | |
| 7,251,524 B1 * | 7/2007 | Hepp et al. | 600/513 |
| 7,272,443 B2 * | 9/2007 | Min et al. | 607/17 |
| 7,410,467 B2 | 8/2008 | Cooper | |
| 7,483,743 B2 | 1/2009 | Mann | |
| 7,488,290 B1 * | 2/2009 | Stahmann et al. | 600/485 |
| 7,590,449 B2 | 9/2009 | Mann | |
| 7,616,991 B2 | 11/2009 | Mann | |
| 2001/0051774 A1 | 12/2001 | Littrup | |
| 2002/0002389 A1 | 1/2002 | Bradley | |
| 2002/0022785 A1 | 2/2002 | Romano | |
| 2003/0083712 A1 | 5/2003 | Rueter | |
| 2003/0220556 A1 | 11/2003 | Porat et al. | |
| 2004/0015196 A1 | 1/2004 | Holmstrom | |
| 2004/0059220 A1 | 3/2004 | Mourad | |
| 2004/0064161 A1 | 4/2004 | Gunderson | |
| 2004/0215097 A1 | 10/2004 | Wang | |
| 2004/0220640 A1 | 11/2004 | Burnes | |
| 2004/0230112 A1 | 11/2004 | Scholz | |
| 2005/0124908 A1 | 6/2005 | Belalcazar | |
| 2005/0215914 A1 * | 9/2005 | Bornzin et al. | 600/508 |
| 2005/0283091 A1 | 12/2005 | Kink | |
| 2006/0025828 A1 | 2/2006 | Armstrong | |
| 2006/0129196 A1 | 6/2006 | Dong | |
| 2006/0135886 A1 | 6/2006 | Lippert | |
| 2006/0184060 A1 | 8/2006 | Belalcazar | |
| 2006/0235480 A1 | 10/2006 | Schecter | |
| 2006/0241512 A1 | 10/2006 | Kwok | |
| 2006/0293609 A1 | 12/2006 | Stahmann | |
| 2008/0009759 A1 * | 1/2008 | Chetham | 600/526 |
| 2008/0033498 A1 * | 2/2008 | Mann et al. | 607/23 |
| 2008/0221477 A1 | 9/2008 | Olson | |
| 2009/0018597 A1 * | 1/2009 | Wenzel et al. | 607/23 |
| 2009/0287267 A1 * | 11/2009 | Wenzel et al. | 607/9 |

FOREIGN PATENT DOCUMENTS

| | | |
|---|---|---|
| WO | WO 96/19260 | 6/1996 |
| WO | WO 98/07467 | 2/1998 |
| WO | WO 0113792 A1 | 3/2001 |
| WO | WO 0132260 A1 | 5/2001 |
| WO | WO 01/87410 A2 | 11/2001 |
| WO | WO 01/87410 A3 | 11/2001 |
| WO | WO2004096041 A2 | 11/2004 |
| WO | WO2004096041 A3 | 11/2004 |
| WO | WO2004105862 | 12/2004 |

OTHER PUBLICATIONS

Non-Final Office Action mailed Jun. 10, 2009: Related U.S. Appl. No. 11/684,677.

Non-Final Office Action mailed May 27, 2009: Related U.S. Appl. No. 11/684,681.

Non-Final Office Action mailed Apr. 6, 2009: Related U.S. Appl. No. 11/558,101.

Non-Final Office Action mailed Feb. 3, 2009: Related U.S. Appl. No. 11/557,851.

Non-Final Office Action mailed May 29, 2009: Related U.S. Appl. No. 11/557,870.

Non-Final Office Action mailed Jun. 10, 2009: Related U.S. Appl. No. 11/557,882.

Non-Final Office Action mailed Jun. 19, 2009 Related U.S. Appl. No. 11/684,664.

Non-Final Office Action mailed Jun. 22, 2009 Related U.S. Appl. No. 11/684,670.

Non-Final Office Action mailed Jun. 23, 2009 Related U.S. Appl. No. 11/558,088.

Non-Final Office Action mailed May 17, 2010: Related U.S. Appl. No. 11/842,109.

Non-Final Office Action mailed Aug. 18, 2009: Related U.S. Appl. No. 11/842,133.

Final Office Action mailed Mar. 8, 2010: Related U.S. Appl. No. 11/842,133.

* cited by examiner

SYSTEM AND METHOD FOR ESTIMATING CARDIAC PRESSURE USING PARAMETERS DERIVED FROM IMPEDANCE SIGNALS DETECTED BY AN IMPLANTABLE MEDICAL DEVICE

RELATED APPLICATIONS

This application is a Continuation-in-Part of U.S. patent application Ser. No. 11/558,101 entitled "Systems and Methods to Monitor and Treat Heart Failure Conditions" and claims priority therefrom.

This application is also related to U.S. Provisional Patent Application No. 60/787,884, filed Mar. 31, 2006 entitled "Tissue Characterization Using Intracardiac Impedances with an Implantable Lead System."

This application is also related to the following U.S. patent application Ser. Nos.:

11/557,851, filed Nov. 8, 2006;

11/557,870, filed Nov. 8, 2006;

11/557,882, filed Nov. 8, 2006; and

11/558,088, filed Nov. 9, 2006;

each entitled "Systems and Methods to Monitor and Treat Heart Failure Conditions." Each of the foregoing applications is fully incorporated by reference herein, including the appendices thereof.

FIELD OF THE INVENTION

The invention relates generally to implantable medical devices such as pacemakers and implantable cardioverter defibrillators (ICDs) and in particular to techniques for estimating cardiac pressure (particularly left atrial pressure (LAP)) to detect and evaluate heart failure and related conditions.

BACKGROUND OF THE INVENTION

Heart failure is a debilitating disease in which abnormal function of the heart leads to inadequate blood flow to fulfill the needs of the tissues and organs of the body. Typically, the heart loses propulsive power because the cardiac muscle loses capacity to stretch and contract. Often, the ventricles do not adequately fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds cardiac muscle causing the ventricles to grow in volume in an attempt to pump more blood with each heartbeat, i.e. to increase the stroke volume. This places a still higher demand on the heart's oxygen supply. If the oxygen supply falls short of the growing demand, as it often does, further injury to the heart may result, typically in the form of myocardial ischemia or myocardial infarction. The additional muscle mass may also stiffen the heart walls to hamper rather than assist in providing cardiac output. Often, electrical and mechanical dyssynchronies develop within the heart such that the various chambers of the heart no longer beat in a synchronized manner, degrading overall cardiac function. A particularly severe form of heart failure is congestive heart failure (CHF) wherein the weak pumping of the heart or compromised filling leads to build-up of fluids in the lungs and other organs and tissues.

Many patients susceptible to CHF, particularly the elderly, have pacemakers, ICDs or other implantable medical devices implanted therein, or are candidates for such devices. Accordingly, it is desirable to provide techniques for detecting and tracking CHF using such devices. One particularly effective parameter for detecting and tracking CHF is cardiac pressure, particularly LAP, i.e. the blood pressure within the left atrium of the patient. Reliable detection of LAP would not only permit the implanted device to track CHF for diagnostic purposes but to also control therapies applied to address CHF such as cardiac resynchronization therapy (CRT). CRT seeks to normalize asynchronous cardiac electrical activation and the resultant asynchronous contractions by delivering synchronized pacing stimulus to the ventricles using pacemakers or ICDs equipped with biventricular pacing capability. The pacing stimulus is typically synchronized so as to help to improve overall cardiac function. This may have the additional beneficial effect of reducing the susceptibility to life-threatening tachyarrhythmias. CRT and related therapies are discussed in, for example, U.S. Pat. No. 6,643,546 to Mathis, et al., entitled "Multi-Electrode Apparatus And Method For Treatment Of Congestive Heart Failure"; U.S. Pat. No. 6,628,988 to Kramer, et al., entitled "Apparatus And Method For Reversal Of Myocardial Remodeling With Electrical Stimulation"; and U.S. Pat. No. 6,512,952 to Stahmann, et al., entitled "Method And Apparatus For Maintaining Synchronized Pacing". Reliable estimates of LAP derived from impedance signals would also allow the dosing of heart failure medications (such as diuretics) to be properly titrated so as to minimize the number of episodes of acute heart failure decompensation. Another advantage to providing reliable estimates of LAP from impedance signals is that physicians are more familiar with LAP values. Hence, LAP estimates could be provided to the physician via diagnostic displays, rather than raw impedance signal values, which the physicians might find difficult to interpret.

However, LAP is a difficult parameter to detect since it is not clinically appealing to place a blood pressure sensor directly in the left atrium due to the chronic risk of thromboembolic events, as well as risks associated with the transseptal implant procedure itself. Accordingly, various techniques have been developed for estimating LAP based on other parameters that can be more safely sensed by a pacemaker or ICD. In this regard, some particularly promising techniques have been developed that use electrical impedance signals to estimate LAP. For example, impedance signals can be sensed along a sensing vector passing through the left atrium, such as between an electrode mounted on a left ventricular (LV) lead and another electrode mounted on a right atrial (RA) lead. The sensed impedance is affected by the blood volume inside the left atrium, which is in turn reflected by the pressure in the left atrium. Accordingly, there is a correlation between the sensed impedance and LAP, which can be exploited to estimate LAP and thereby also track CHF. See, for example, techniques described in the related patent applications, cited above. See also, U.S. patent application Ser. No. 11/558,194, by Panescu et al., entitled "Closed-Loop Adaptive Adjustment of Pacing Therapy based on Cardiogenic Impedance Signals Detected by an Implantable Medical Device", which is incorporated by reference herein if (filed contemporaneously herewith or filed previously hereto.)

Although electrical impedance can be used to estimate LAP, it is difficult to reliably calibrate such impedance-based estimation techniques. That is, it is difficult to accurately and reliably convert detected electrical impedance values into actual LAP values. Accordingly, it would be highly desirable to provide improved techniques for calibrating impedance-based LAP estimation techniques and it is to that end that certain aspects of the present invention are directed. More broadly, it would be desirable to provide improved techniques for estimating LAP or other cardiac pressure parameters for use in controlling therapy or for providing diagnostic information, and it is to that end that other aspects of the present invention are also directed.

SUMMARY OF THE INVENTION

In accordance with an exemplary embodiment, a method is provided for estimating cardiac pressure within a patient using an implantable medical device. Broadly, an electrical field (such as the electrical field of an impedance detection pulse) is applied to tissues of the patient, including cardiac tissues. A parameter influenced by the electrical field is measured, wherein the parameter is affected by cardiac pressure. Examples include impedance values (Z) or conductance values (G) measured in response to an impedance detection pulse. Then, cardiac pressure is estimated within the patient by applying predetermined conversion factors to the measured parameter. In one example, an electrical impedance (Z) signal is detected within the patient in response to a series of impedance detected pulses. The impedance (Z) signal is detected along a sensing vector wherein impedance is affected by LAP or other cardiac pressure values. One or more predetermined parameters are derived from the electrical impedance (Z) signal, such as an electrical conductance (G) value, a cardiogenic pulse amplitude value, a circadian rhythm pulse amplitude, or a signal morphology fractionation parameter. Predetermined conversion factors are then input for converting the parameters derived from the electrical impedance signal (Z) to LAP values or other cardiac pressure values. The conversion factors may be, for example, slope and baseline values derived using, e.g., linear regression techniques. Then, LAP or other cardiac pressure values are estimated within the patient by applying the conversion factors to the parameters derived from the electrical impedance (Z) signal. In some implementations, particular components of an initial raw impedance signal ($Z_0$) are exploited, such as a high-frequency cardiogenic impedance signal ($Z_C$) representative of the beating of the heart of the patient, a low-frequency respiratory impedance signal ($Z_R$) representative of the respiration of the patient, or an ultra-low frequency circadian impedance signal representative of daily variations in the raw impedance signal ($Z_0$).

In a first illustrative example, the parameter derived from the electrical impedance signal (Z) is an electrical conductance (G) value. The electrical conductance (G) is the reciprocal of the electrical impedance (Z) and may be derived, e.g., from the raw impedance signal ($Z_0$), though either the respiratory impedance ($Z_R$) signal or the cardiogenic impedance ($Z_C$) signal can alternatively be used. Alternatively, conductance may be measured directly within the patient without necessarily first detecting impedance. In any case, the predetermined conversion factors to be used are slope and baseline values ($Slope_G$ and $Baseline_G$) representative of a linear relationship between conductance and cardiac pressure. Cardiac pressure is estimated using:

$$\text{Cardiac Pressure}=G*Slope_G+Baseline_G.$$

The cardiac pressure estimated in this example (and in the other examples described herein) is an effective intracardiac pressure ($P_{eff}$) not an absolute pressure. It represents the absolute intracardiac pressure less intrathoracic pressure:

$$P_{eff}=P_{intracardiac}-P_{intrathoracic}$$

That is, the effective pressure is a type of gauge pressure. Unless otherwise noted, all estimated cardiac pressure values discussed herein, particularly estimated LAP (eLAP), are effective pressure values. In some techniques described herein, such as techniques where the Valsalva maneuver is exploited to reduce intracardiac pressure within the patient for the calibration purposes, the distinction between effective pressure and absolute pressure is particularly important and effective pressure should be used. In those examples, the term effective LAP will be used as a reminder that effective pressures are used. In any case, effective pressure values are typically more useful from a clinical perspective than absolute pressure values.

Typically, the conductance (G) values are derived from raw impedance values ($Z_0$) measured along a sensing vector through the left atrium of the heart of the patient such that the resulting cardiac pressure value is an estimated LAP value (eLAP), which may be obtained by calculating:

$$eLAP=G*Slope_G+bLAP_G;$$

wherein $Slope_G$ and $bLAP_G$ are values derived specifically for converting conductance values to LAP estimates. LAP is believed to be directly proportional to conductance. In some implementations, a series of individual conductance values (G(t)) are detected substantially in real-time (based on a time-varying impedance signals (Z(t)) so as to permit changes in LAP to be tracked substantially in real-time as well.

In the first illustrative example, the slope and baseline values ($Slope_G$ and $bLAP_G$) are determined during an initial calibration procedure based on the assumption that there is a linear relationship between conductance (G) and LAP. To calibrate the slope and baseline values for a particular patient, a first conductance calibration value ($G_1$) and a corresponding first cardiac pressure calibration value ($LAP_1$) are measured within the patient at a first point in time. Then, a second conductance calibration value ($G_2$) and a corresponding second cardiac pressure calibration value ($LAP_2$) are measured at a second point time within the patient. The first and second pressure calibration values ($LAP_1$, $LAP_2$) may be measured within the patient using, e.g., a Swan-Ganz catheter equipped to measure pulmonary capillary wedge pressure (PCWP). The times are chosen such that the first and second cardiac pressure values ($LAP_1$, $LAP_2$) differ substantially from one another (and so the conductance calibration values also differ substantially from one another). In one particular example, the first calibration values ($G_1$, $LAP_1$) are detected while the patient is at rest; whereas the second calibration values ($G_2$, $LAP_2$) are detected while the patient is subject to a condition significantly affecting cardiac pressure, such as isometric muscle contraction, vasodilatation, vasoconstriction, rapid pacing or performance of the Valsalva maneuver by the patient. The slope value is then calibrated by calculating:

$$Slope_G=(LAP_2-LAP_1)/(G_2-G_1).$$

The baseline value is calibrated by calculating:

$$bLAP_G = Pressure_2 - Slope_G * G_1.$$

Alternatively, a plurality of calibration values can instead be obtained within the patient, with the slope and baseline values then calculated for that particular patient using linear regression techniques. In still other implementations, calibration values are instead obtained within test subjects, with the calibration values then employed to estimate LAP within other patients. For example, a plurality of calibration values can be obtained within a population of test subjects (particularly ones in which heart failure is progressing), with the slope and baseline values then calculated using linear regression techniques from the data obtained from the test subjects. By using test subjects in which heart failure is progressing, LAP therefore likewise increases within the test subjects, yielding a range of pressure values suitable for linear regression analysis. The slope and baseline values obtained from the test subjects can be used, at least, as starting values for use in estimating LAP within other patients, with those parameters then potentially optimized for use in the particular patient. Still further, linear models relating cardiac pressure and conductance need not necessarily be used, i.e. more sophisticated correlation models may instead by used. Linear models are preferred in view of their simplicity.

The slope value, once determined, is less likely to change over time within a particular patient. However, the baseline value might change. Accordingly, it may be desirable within some patients to occasionally re-calibrate the baseline value. To re-calibrate the baseline value, an additional conductance calibration value ($G_N$) is measured while the patient performs a Valsalva maneuver. During the Valsalva maneuver, the chambers of the heart are substantially emptied of blood such that the effective cardiac blood pressure, particularly effective LAP or effective right atrial pressure (RAP), is reduced to near zero secondary to reduced venous return, especially in patients that have at rest moderate to low cardiac filling pressures (<20 mmHg) with the absence of significant diastolic dysfunction or non-compliance of the heart. Under the assumption that the effective LAP drops to zero in the late Phase II of the Valsalva maneuver (i.e., during the interval from 5 seconds to 10 seconds following the initiation of the strain), the baseline value to be updated by the implanted device using only the newly detected conductance value, i.e. $bLAP_G$ may be updated using:

$$bLAP_G = -Slope_G *$$

In other implementations, both the slope and baseline values are re-calibrated by the implanted device based on newly detected conductance values. In still other implementations, to account for the fact that effective LAP does not reach completely zero during the Valsalva maneuver in some patients (such as heart failure patients with high cardiac filling pressures >20 mmHg and/or with poor cardiac compliance), an additional correction term may be obtained during initial calibration that is used to correct or adjust the re-calibrated values. Also, note that, if the lungs are "dry" (i.e., without congestion) and there is only a change in pulmonary venous volume with emptying during Valsalva, conductance should fall to a new zero baseline value as well. If there is extravascular interstitial pulmonary fluid accumulation, and the impedance vector primarily passes through the lung, impedance may not change substantially during Valsalva because the overall amount of interstitial lung fluid does not change substantially, only by the intravascular fraction of blood emptying from the pulmonary veins. Preferably, re-calibration is performed while the patient is clinically stable and the lungs are "dry". Also, by using an impedance vector passing through the left atrium, the affect of any interstitial pulmonary fluids on the detected impendence/conductance values is minimized. Still further, within at least some patients, even when using an impedance vector passing through a cardiac chamber, changes in impedance during Valsalva may be somewhat unpredictable because of changing intra-electrode distances and changing fluid volumes. Accordingly, in at least some patients, Valsalva-based re-calibration techniques may not achieve precise calibration due to these factors. Within those patients, other re-calibration techniques are preferably used, which do not necessarily exploit the Valsalva maneuver.

In a second illustrative example of the invention, the parameter derived from the electrical impedance signal (Z) is the cardiogenic pulse amplitude value derived from the cardiogenic impedance signal ($Z_C$). Alternatively, the cardiogenic pulse amplitude may be obtained without necessarily first detecting impedance by, for example, detecting conductance instead. In any case, cardiac pressure is then estimated based on the cardiogenic pulse amplitude value using conversion factors calibrated for converting cardiogenic pulse amplitudes to cardiac pressure values, particularly LAP values. In one example, it is assumed that cardiogenic pulse amplitude is inversely proportional to LAP (when the cardiogenic pulse amplitude is derived from an impedance signal sensed along a vector passing through the left atrium.) Accordingly, a linear model relating cardiogenic pulse amplitude to LAP may be exploited. That is, to perform the actual conversion of cardiogenic pulse amplitudes to LAP values, slope and baseline values are used, calibrated for use with cardiogenic pulse amplitudes. More specifically, LAP may be estimated by calculating:

$$eLAP = Cardiogenic\_Pulse\_Amplitude * Slope_{CARDIOGENIC} + bLAP_{CARDIOGENIC}$$

wherein Cardiogenic_Pulse_Amplitude is an amplitude value derived from the impedance signal (Z) and $Slope_{CARDIOGENIC}$ and $bLAP_{CARDIOGENIC}$ are conversion values derived specifically for use converting cardiogenic pulse amplitude values to LAP values. The amplitude value may be, e.g., an individual value or an average of individual values or some other combination of values. The various techniques summarized above may be used to calibrate and re-calibrate the cardiogenic pulse amplitude-based conversion values for use with particular patients. In some implementations, individual cardiogenic pulse amplitude values are detected substantially in real-time so as to permit changes in LAP to be tracked substantially in real-time as well.

In a third illustrative example, the parameter derived from the electrical impedance signal (Z) is the circadian pulse amplitude value derived from the circadian component of the raw impedance signal ($Z_O$), though the circadian pulse amplitude could instead be derived from, e.g., the respiratory impedance ($Z_R$) signal. Alternatively, the circadian pulse amplitude may be obtained without necessarily first detecting impedance by, for example, detecting conductance instead. In the impedance-based example, the circadian pulse amplitude represents the daily variation in the impedance signal and is preferably calculated once per day. Within healthy patients, there is typically a significant daily variation in impedance and so the circadian pulse amplitude may be significant, e.g. 20 ohms or more. Within patients suffering from heart failure, however, there is typically little or no significant daily variation in impedance and so the circadian pulse amplitude is at or near zero. Hence, progression of heart failure correlates with a decrease in circadian pulse amplitudes. As already noted, there is also a correlation with LAP and heart failure, i.e. LAP increases due to progression of heart failure. Accordingly, there is a correlation between decreasing circadian pulse amplitudes and increasing LAP. In one example, it is assumed that circadian pulse amplitude is inversely proportional to LAP. In that example, cardiac pressure is estimated based on the circadian pulse amplitude using conversion factors calibrated for converting circadian pulse amplitudes to cardiac pressure values, particularly LAP values. To perform the actual conversion of circadian pulse amplitudes to LAP values, slope and baseline values may be used, calibrated for use with circadian pulse amplitudes. That is, LAP may be estimated by calculating:

$$eLAP = Circadian\_Pulse\_Amplitude * Slope_{CIRCADIAN} + bLAP_{CIRCADIAN}$$

wherein Circadian_Pulse_Amplitude is an individual circadian pulse amplitude value derived from the impedance signal over a twenty-four hour period and wherein $Slope_{CIRCADIAN}$ and $bLAP_{CIRCADIAN}$ are conversion values derived specifically for use converting circadian pulse amplitude values to LAP values. Unlike the embodiments summarized above wherein real-time tracking of LAP is typically feasible, circadian pulse amplitudes are not used to track changes in LAP in real-time. Rather, circadian pulse amplitudes are tracked over relative long periods of time (e.g., weeks or months) to detect gradual changes in LAP within the patient brought on by heart failure or other factors. Any of a variety of techniques may be used to calibrate and re-calibrate the circadian pulse amplitude-based conversion values for use with particular patients. For example, linear regression techniques may be used to derive suitable slope and baseline values from a plurality of pressure and circadian pulse amplitude calibration values obtained from test subjects.

In a fourth illustrative example, the parameter derived from the electrical impedance signal (Z) is a fractionation value derived from the morphology of the cardiogenic impedance signal ($Z_C$). Alternatively, the fractionation value may be obtained without necessarily first detecting impedance by, for example, detecting conductance instead. In the impedance-based example, the fractionation value represents the degree of fractionation in a cardiogenic component of the impedance signal, i.e. that portion of the impedance signal that varies in accordance with the beating of the heart. Fractionation increases due to increasing mechanical dyssynchrony and abnormal transvalvular flow patterns within the heart arising due to heart failure. As already noted, LAP also typically increases due to heart failure. Accordingly, there is a correlation between increasing fractionation and increasing LAP. In one example, it is assumed that increasing fractionation of the cardiogenic component of the impedance signal is directly proportional to LAP. In that example, LAP may be estimated based on fractionation using conversion factors calibrated for converting fractionation values to cardiac pressure values, particularly LAP values. To perform the actual conversion of fractionation values to LAP values, slope and baseline values may be used, calibrated for use with fractionation values. That is, LAP may be estimated by calculating:

$$eLAP = Fractionation\_Index * Slope_{FRAC} + bLAP_{FRAC}$$

wherein Fractionation_Index is an index derived from the cardiogenic impedance signal over an extended period of time and wherein $Slope_{FRAC}$ and $bLAP_{FRAC}$ are conversion values derived specifically for use in converting Fractionation_Index values to LAP values. The Fractionation_Index is a measure of the complexity of the morphology of the cardiogenic impedance signal. As the cardiogenic impedance signal becomes more complex the Fractionation_Index increases. Patients with a low LAP have a cardiogenic impedance signal that is monophasic or biphasic, while patients with a high LAP tend to have triphasic or multiphasic cardiogenic impedance signals. The Fractionation_Index may be derived in more than one way from the cardiogenic impedance signal. For example, the frequency content of the cardiogenic impedance signal may be used as the Fractionation_Index, or more simply the number of peaks and troughs counted within each cardiac cycle may also be used as a Fractionation_Index. Similar to the Cardiogenic_Pulse_Amplitude technique summarized above, the Fractionation_Index may be computed on a beat-by-beat basis to permit changes in LAP to be tracked substantially in real-time as well. Alternatively, the Fractionation_Index can be computed over longer periods of time to track long-term changes in LAP. Any of a variety of techniques may be used to calibrate and re-calibrate the fractionation-based conversion values for use with particular patients, such as linear regression applied to calibration values obtained from test subjects. Fractionation may also be exploited in connection with the circadian impedance signal discussed above, i.e. an increase in fractionation of the circadian impedance is correlated with an increase in LAP and can be used to estimate LAP.

Thus, various techniques are provided for estimating LAP for use, e.g., in detecting and tracking heart failure. Individual implantable systems may be equipped to perform some or all of these techniques. In some examples, LAP is determined by combining estimates derived from the various individual techniques. Heart failure is then detected based on the combined LAP estimate. Upon detecting of the onset of heart failure, appropriate warning signals may be generated for alerting the patient to consult a physician. The warning signals can include "tickle" warning signals applied to subcutaneous tissue and short range telemetry warning signals transmitted to a warning device external to the patient such as a bedside monitor. The warning signals, as well as appropriate diagnostic information (such as the estimated LAP values), are preferably forwarded to the physician by the bedside monitor. Therapy may also be automatically applied or modified by the implanted system in response to heart failure, depending upon the capabilities of the system. For example, if the device is equipped to perform CRT, then CRT pacing may be initiated or otherwise controlled based on LAP. Also, if the implanted system is equipped with a drug pump, appropriate medications (such as diuretics) potentially may be administered directly to the patient, depending upon the programming of the system. Alternatively, the estimated LAP may be presented directly to the patient using a handheld or a bedside monitor, so that the patients may utilize the estimated LAP reading to self-titrate oral dosages of heart failure medications based on a sliding scale prescription that was provided to the patient in advance. This concept is similar to the self-titration of insulin dosage based on a measured blood sugar from a glucometer using a prescribed insulin sliding scale.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Medical System

Figure 1:
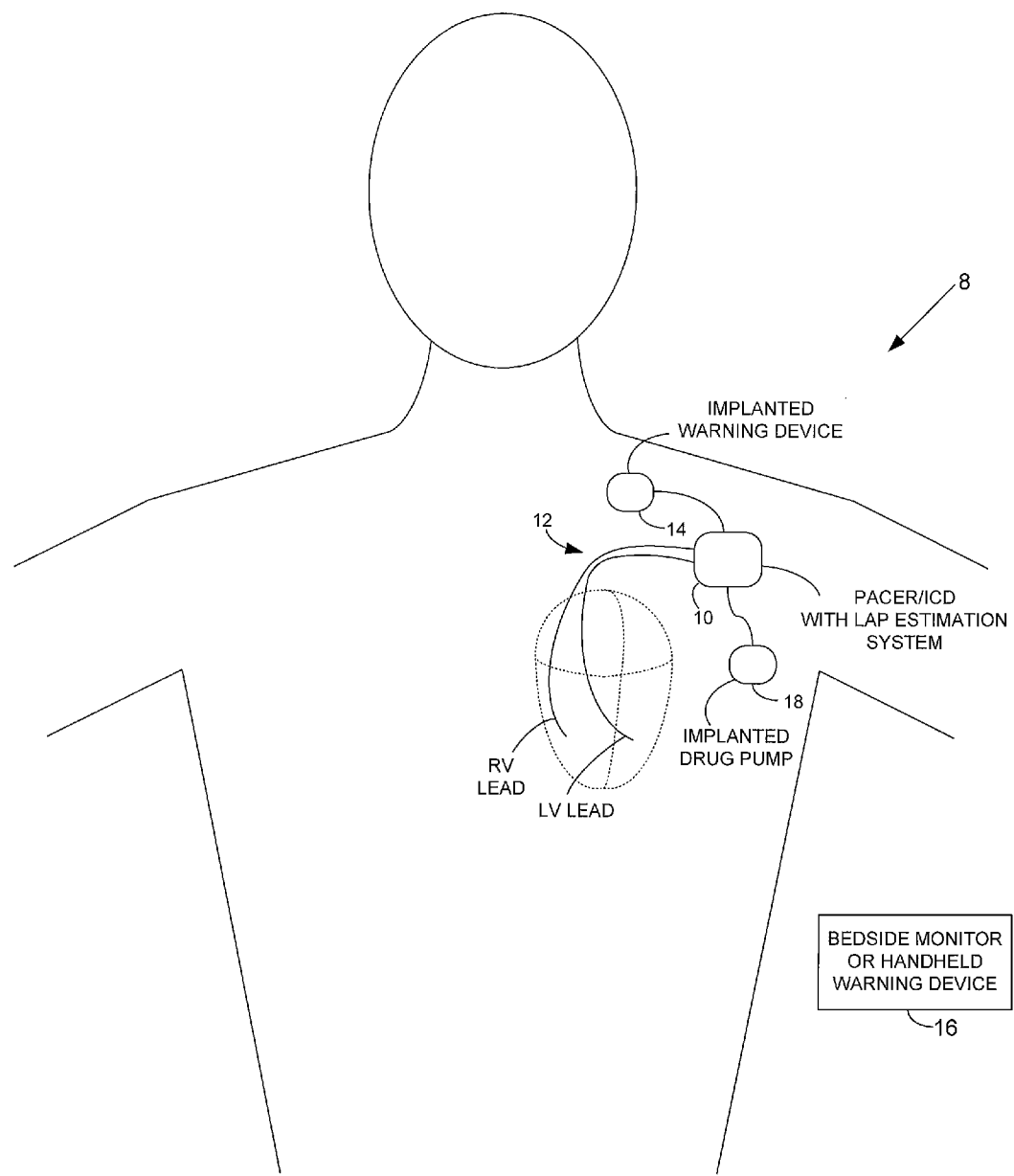
FIG. 1 is a stylized representation of an exemplary implantable medical system equipped with LAP estimation system.
Figure 19:
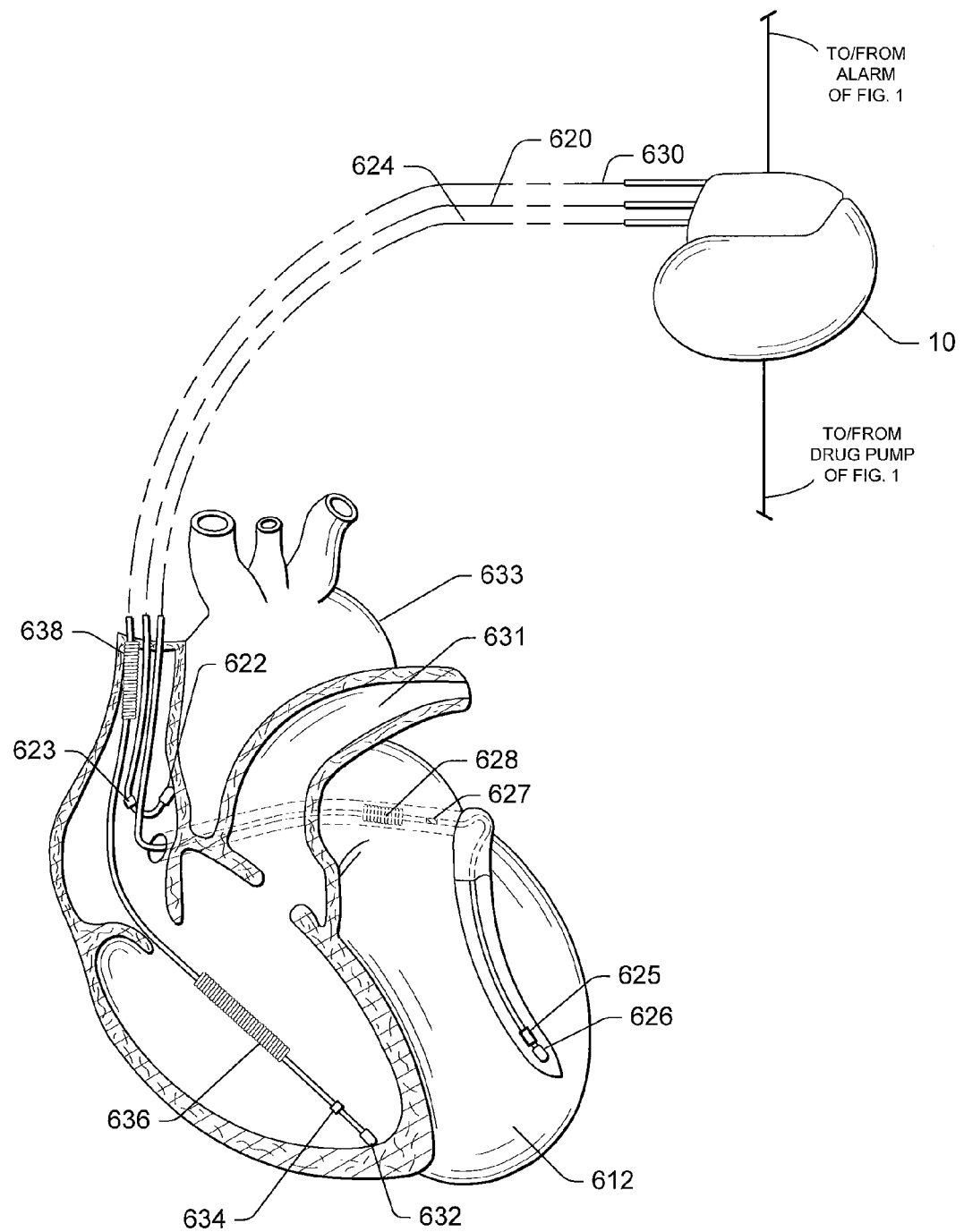
FIG. 19 is a simplified, partly cutaway view, illustrating the pacer/ICD of FIG. 1 along with at full set of leads implanted in the heart of the patient.

FIG. 1 provides a stylized representation of an exemplary implantable pacing medical system 8 capable of detecting electrical impedance signals and estimating LAP based on the impedance signals. To this end, implantable system 8 includes a pacer/ICD 10 or other cardiac stimulation device that incorporates internal components (shown individually in FIG. 20) for detecting one or more impedance signals using electrodes mounted to a set of sensing/pacing leads 12 and for estimating LAP or other cardiac pressure parameters based on various parameters derived from the impedance signals. In FIG. 1, only two leads are shown. A more complete set of leads is illustrated in FIG. 19, which is discussed below. Within the exemplary implementations described herein, LAP is estimated based on one or more of: electrical conductance values, cardiogenic pulse amplitudes, circadian rhythm pulse amplitudes, or signal morphology fractionation index values, each derived from the impedance signals detected by the pacer/ICD. Predetermined conversion factors stored within the pacer/ICD are used to convert the various parameters derived from the electrical impedance signal into LAP values or other appropriate cardiac pressure values. The conversion factors may be, for example, slope and baseline values derived during an initial calibration procedure performed by an external system, such as an external programmer (FIG. 21.) As will be explained, the baseline value may be periodically re-calibrated by the pacer/ICD itself. The slope value is assumed to remain substantially unchanged such that re-calibration of the slope is typically not required.

The pacer/ICD is also equipped to track changes in the estimated LAP values so as to detect and track CHF. CRT therapy may be initiated and controlled by the pacer/ICD, accordingly. Techniques for performing CRT are discussed in the patents to Mathis, et al., Kramer, et al., to Stahmann, et al., cited above. CRT parameters may be adaptively adjusted based on the impedance signals to improve the effectiveness of CRT using techniques set forth in the Panescu et al. patent application, "Closed-Loop Adaptive Adjustment of Pacing Therapy based on Cardiogenic Impedance Signals Detected by an Implantable Medical Device", cited above. Additionally or alternatively, the pacer/ICD can issue warning signals, if warranted. For example, if the estimated LAP exceeds a threshold indicative of CHF, warning signals may be generated to warn the patient, using either an internal warning device 14 or an external bedside monitor/handheld warning device 16. Internal warning device 14 may be a vibrating device or a "tickle" voltage device that, in either case, provides perceptible stimulation to the patient to alert the patient so that the patient may consult a physician. In one example, once the tickle warning is felt, the patient positions an external warning device above his or her chest. The handheld device receives short-range telemetry signals from the implanted device and provides audible or visual verification of the warning signal. The handheld warning device thereby provides confirmation of the warning to the patient along with a display of the estimated LAP, who may be otherwise uncertain as to the reason for the internally generated warning signal. For further information regarding this warning/notification technique, see U.S. patent application Ser. No. 11/043,612, of Kil et al., filed Jan. 25, 2005, entitled "System and Method for Distinguishing Among Ischemia, Hypoglycemia and Hyperglycemia Using an Implantable Medical Device."

If a bedside monitor is provided, the bedside monitor provides audible or visual alarm signals to alert the patient as well as textual or graphic displays. In addition, diagnostic information pertaining to the deteriorating cardiac condition is transferred to the bedside monitor or is stored within the pacer/ICD for subsequent transmission to an external programmer (not shown in FIG. 1) for review by a physician or other medical professional. The physician may then prescribe any other appropriate therapies to address the condition. The physician may also adjust the operation of the pacer/ICD to activate, deactivate or otherwise control any therapies that are automatically applied. The bedside monitor may be directly networked with a centralized computing system, such as the HouseCall™ system of St. Jude Medical, for immediately notifying the physician of any significant increase in LAP. Networking techniques for use with implantable medical systems are set forth, for example, in U.S. Pat. No. 6,249,705 to Snell, entitled "Distributed Network System for Use with Implantable Medical Devices".

In addition to CRT, other forms of therapy may also be controlled by the pacer/ICD in response to changes in LAP. In this regard, if the implanted system is equipped with a drug pump, appropriate medications may be automatically administered upon detection of a significant increase in LAP due to heart failure. For example, heart failure medications may be delivered directly to the patient via the drug pump, if warranted. Alternatively, if a drug pump is not available, the patient may be provided with instructions depending on the estimated LAP as to what dosage to take for various heart failure medications. Exemplary heart failure medications include angiotensin-converting enzyme (ACE) inhibitors, diuretics, digitalis and compounds such as captopril, enalapril, lisinopril and quinapril. Depending upon the particular medication, alternative compounds may be required for use in connection with an implantable drug pump. Routine experimentation may be employed to identify medications for treatment of heart failure or other conditions that are safe and effective for use in connection with an implantable drug pump. Dosages may be titrated based upon the severity of heart failure as determined from LAP.

Various techniques may be employed to confirm the detection of heart failure (or other medical conditions) made by the pacer/ICD based on the analysis of the impedance signals before drug therapy is delivered. Exemplary heart failure detection/evaluation techniques are set forth in: U.S. Pat. No. 6,748,261, entitled "Implantable medical device for and Method of Monitoring Progression or Regression of Heart Disease by Monitoring Interchamber Conduction Delays"; U.S. Pat. No. 6,741,885, entitled "Implantable Cardiac Device for Managing the Progression of Heart Disease and Method"; U.S. Pat. No. 6,643,548, entitled "Implantable medical device for Monitoring Heart Sounds to Detect Progression and Regression of Heart Disease and Method Thereof"; U.S. Pat. No. 6,572,557, entitled "System and Method for Monitoring Progression of Cardiac Disease State using Physiologic Sensors"; and U.S. Pat. No. 6,480,733, entitled "Method for Monitoring Heart Failure", each assigned to Pacesetter, Inc.

Hence, FIG. 1 provides an overview of an implantable medical system capable of estimating LAP based on impedance signals, delivering any appropriate warning/notification signals, and selectively delivering medications, when warranted. Embodiments may be implemented that do not necessarily perform all of these functions. For example, embodiments may be implemented that estimate LAP but do not automatically initiate or adjust therapy. Moreover, systems provided in accordance with the invention need not include all of the components shown in FIG. 1. In many cases, for example, the system will include only a pacer/ICD and its leads. Implantable warning devices and drug pumps are not necessarily implanted. Some implementations may employ an external monitor for displaying warning signals without any internal warning device. These are just a few exemplary embodiments. No attempt is made herein to describe all possible combinations of components that may be provided in accordance with the general principles of the invention. In addition, note that the particular locations of the implanted components shown in FIG. 1 are merely illustrative and may not necessarily correspond to actual implant locations. Although internal signal transmission lines provided are illustrated in FIG. 1 for interconnecting the various implanted components, wireless signal transmission may alternatively be employed.

Overview of LAP Estimation based on Electrical Impedance

Figure 2:
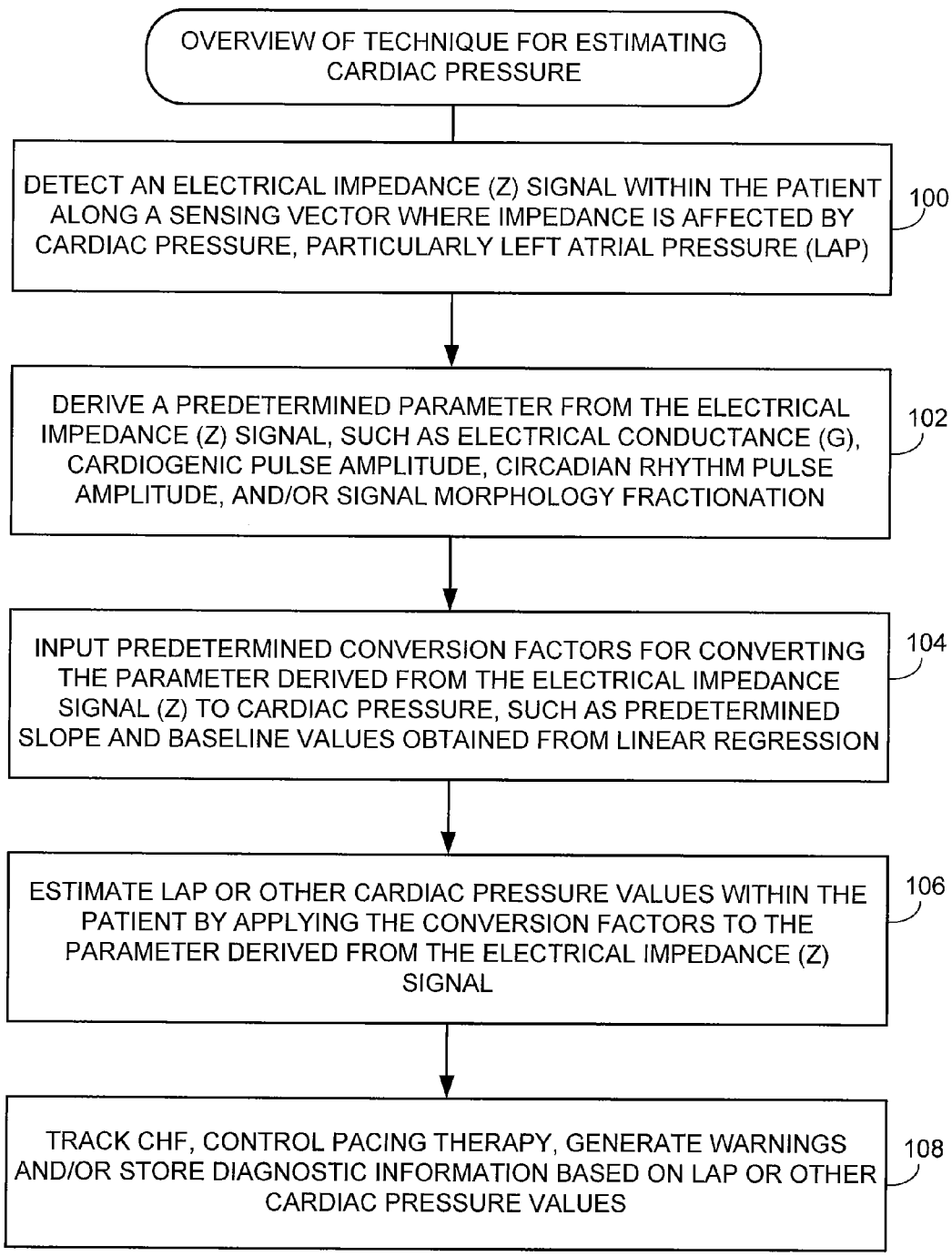
FIG. 2 is a flow diagram providing an overview of LAP estimation techniques that may be performed by the system of FIG. 1.

FIG. 2 provides an overview of the LAP estimation techniques that may be performed by the pacer/ICD of FIG. 1 or other implantable device. Broadly, at steps 101 and 102, a predetermined impedance-based parameter is measured within patient tissues, wherein the parameter is affected by cardiac pressure. At steps 104 and 106, cardiac pressure is then estimated within the patient by applying predetermined conversion factors to the impedance-based parameter. Alternatively, conductance (G) or other suitable electrical parameters can instead be detected. Considering the impedance-based example in more detail, at step 100, the pacer/ICD detects electrical impedance (Z) along a sensing vector where impedance is affected by cardiac pressure, particularly LAP. For example, the cardiogenic impedance signal may be sensed between an LV tip electrode and an RA tip electrode such that the sensing vector passes through the left atrium. However, impedance signals sensed between other electrode pairs, such as the LV lead and the device can, may alternatively be utilized to indirectly estimate LAP under the presumption that, if these electrode pairs span the region containing the blood within pulmonary veins, then a resulting estimate of pulmonary venous pressure may be used as an estimate for LAP.

Impedance signals are obtained by transmitting a current between a pair of electrodes, and subsequently, measuring the voltage between the same or another pair of electrodes. The impedance is calculated as the ratio of the measured voltage to the transmitted current. Preferably, a tri-phasic impedance pulse waveform is employed to sense the impedance signal. The tri-phasic waveform is a frequency-rich, low energy waveform that provides a net-zero charge and a net-zero voltage. An exemplary tri-phasic pulse waveform is described in detail in the related patent applications, cited above. Depending upon the particular sensing vector, it may be appropriate to filter the impedance signal to eliminate or reduce any non-cardiogenic components such as any components arising due to respiration or changes in body position of posture. Bandpass filtering is typically sufficient to filter out respiratory components.

Although the examples described herein are primarily directed to estimating LAP, other cardiac pressure values may alternatively be estimated, such as LVP, by using impedance signals detected using appropriate sensing vectors (e.g., LV-tip electrode to RV-ring electrode or RV-Shock coil). Indeed, multiple impedance signals may be sensed using different sensing vectors passing through different chambers of the heart so as to permit the pacer/ICD to estimate cardiac pressure within different chambers of the heart, assuming appropriate conversion values have been determined and calibrated. To this end, the implanted system may be equipped, e.g., with multiple electrodes per lead or with multiple leads per chamber. Unipolar or bipolar sensing systems may be employed.

Depending upon the implementation, particular components of an initial raw impedance signal ($Z_O$) detected by the pacer/ICD are exploited, such as the high-frequency cardiogenic impedance signal ($Z_C$) representative of the beating of the heart of the patient, the low-frequency respiratory impedance signal ($Z_R$) representative of the respiration of the patient, or the ultra-low frequency circadian impedance signal representative of daily variations in the raw impedance signal ($Z_O$) or the low-frequency respiratory impedance signal ($Z_R$). Note that current state-of-the art pacer/ICDs do not typically include a detection circuit specifically for detecting circadian impedance variations. There is a cardiogenic detection circuit that extracts the cardiogenic component ($Z_C$) of the impedance signal (also referred to as cardiogenic impedance (CI)) from the raw impedance signal ($Z_O$) by substantially filtering out non-cardiogenic components. There is a low frequency detection circuit that extracts the respiratory component ($Z_R$) of the impedance signal (also referred to as respiratory impedance (RI)) by substantially filtering out non-respiratory components. Circadian variations may be detected by storing the raw impedance values over a 24-hour period then processing the recorded raw values to extract circadian variations. In the predecessor applications cited above, the term "low-frequency raw impedance signal" was used to refer to the respiratory impedance signal ($Z_R$). Techniques for detecting or extracting the various components of the initial raw impedance signal are discussed in the cited applications.

At step 102, the pacer/ICD derives one or more predetermined parameters from the detected electrical impedance signals, such as electrical conductance (G), cardiogenic pulse amplitude, circadian rhythm pulse amplitude, or signal morphology fractionation parameters. Examples involving each are discussed below. At step 104, the pacer/ICD inputs predetermined conversion factors from memory for converting the parameter(s) derived from the electrical impedance signal to LAP (or other cardiac pressure values). The conversion factors may be, e.g., predetermined slope and baseline values obtained during a calibration procedure employing linear regression. Different conversion factors are typically required depending upon the particular parameters derived from the electrical impedance signal. That is, different slope and baseline values are used for a conductance-based estimation than for a cardiogenic pulse amplitude-based estimation. In some implementations, the pacer/ICD is equipped to perform only one estimation technique, such as conductance-based estimation, and so the only conversion values stored in memory are conductance-based conversion factors. In other implementations, the pacer/ICD is equipped to perform any or all of the estimation techniques described herein and so the memory of the pacer/ICD stores all of the different conversion factors and retrieves the appropriate factors depending upon the particular estimation technique currently being used, as specified by the programming of the device. LAP values estimated using different techniques may be averaged together.

At step 106, the pacer/ICD then estimates LAP or other cardiac pressure values within the patient by applying the conversion factors retrieved from memory (as step 104) to the parameter(s) derived from the electrical impedance signal (as step 104). When using slope and baseline conversion factors, cardiac pressure may be generally estimated using:

$$Cardiac\ Pressure = Derived\_Parameter * Slope + Baseline$$

where Derived_Parameter represents the parameter derived from the impedance signal, i.e. conductance, cardiogenic pulse amplitude, etc., and Slope and Baseline represent the conversion factors appropriate for use with the particular derived parameter. This formula assumes a linear relationship between cardiac pressure and the derived parameters, which is an appropriate presumption based on the particular parameters discussed herein, at least insofar as estimating LAP is concerned. Routine experimentation may be performed to determine whether a linear relationship is also suitable for use in estimating other particular cardiac pressure values, such as LVP, or is also suitable for use with other parameters that might be derived from the electrical impedance signal besides those specifically mentioned herein. Moreover, it should be understood that linear models need not necessarily be used, i.e. more sophisticated correlation models may instead by employed. Linear models are preferred in view of their simplicity.

At step 108, the pacer/ICD tracks CHF, controls pacing therapy (such as CRT), generates warnings and/or stores diagnostic information based on estimated LAP values or other estimated cardiac pressure values. As already explained, the warnings and/or diagnostic data can be forwarded to a physician for review. Preferably, the diagnostic data includes the estimated LAP values for physician review. This is particularly advantageous since physicians are typically more comfortable reviewing LAP information than raw impedance values. Steps 100-108 may be repeated in a loop so as to update the estimated LAP. Depending upon the particular parameter used to estimate LAP, the estimates may be performed substantially in real-time so as to permit the pacer/ICD to continuously, or at least very frequently, calculate new LAP values. That is, in some implementations, a real-time LAP(t) function may be estimated so as to allow the pacer/ICD to track beat-to-beat changes in LAP. In particular, estimates of LAP based on conductance, on cardiogenic pulse amplitudes, or cardiogenic fractionation may potentially be performed substantially in real-time, assuming the pacer/ICD is appropriately configured. This allows the pacer/ICD to respond promptly to changes within the heart of the patient. Estimates of LAP based on circadian pulse amplitudes are not performed in real-time. Rather, these parameters are tracked over extended periods of time (e.g. days, weeks or months) so as to track longer-term changes in the heart of the patient.

Turning now to FIGS. 3-16, various illustrative embodiments will be described in greater detail.

Exemplary LAP Estimation Techniques

Figure 3:
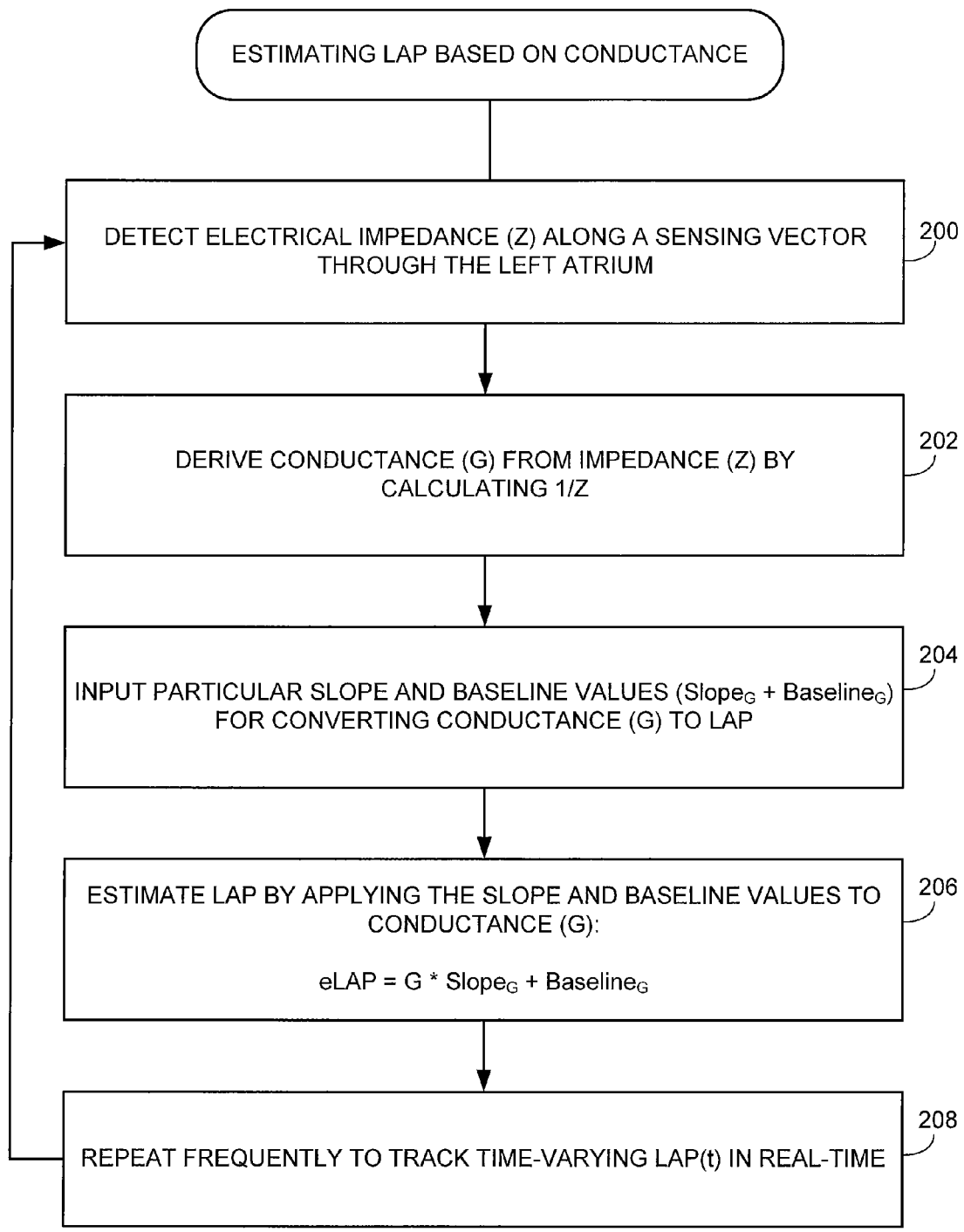
FIG. 3 is a flow diagram summarizing a first illustrative technique wherein LAP is estimated based on electrical conductance, and which may be performed in accordance with the general technique of FIG. 2.

Referring next to FIG. 3, a conductance-based LAP detection example is illustrated. At step 200, the pacer/ICD detects electrical impedance (Z) along a sensing vector through the left atrium and, at step 202, derives conductance (G) from impedance (Z) by calculating 1/Z, i.e. by taking the reciprocal of the impedance. Preferably, the raw impedance signal ($Z_0$) is used to derive conductance, though other impedance signals could instead be used. Alternatively, conductance may be measured directly within the patient without necessarily first detecting impedance. In any case, at step 204, the pacer/ICD inputs the particular slope and baseline values ($Slope_G$+$Baseline_G$) for converting conductance to LAP. These are predetermined conversion values that the pacer/ICD retrieves from memory. Calibration techniques for initially deriving the conversion values will be discussed below with reference to FIGS. 4-10. At step 206, the pacer/ICD estimates LAP by applying the slope and baseline values (input at step 204) to the conductance value (derived at step 202):

$$eLAP = G * Slope_G + Baseline_G$$

As indicated by step 208, the pacer/ICD can repeat steps 200-206 frequently so as to track a time-varying LAP function, i.e. LAP(t).

Figure 4:
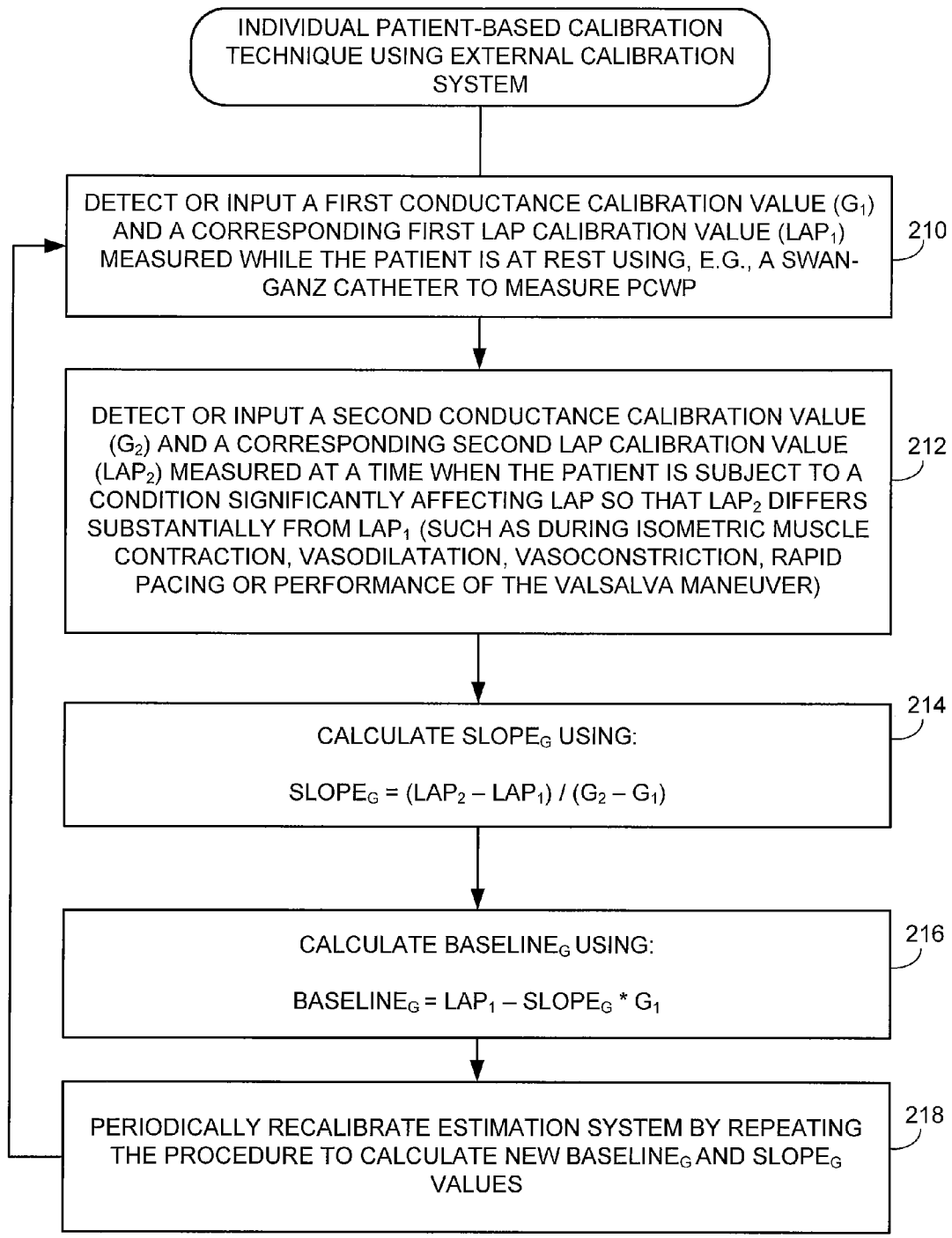
FIG. 4 is a flow diagram illustrating an exemplary procedure for calibrating the LAP-based technique of FIG. 3 using calibration parameters obtained within the patient in which the system is implanted.

A variety of techniques may be used to initially determine and subsequently adjust the conversion values ($Slope_G$+ $Baseline_G$), i.e. to calibrate the conductance-based estimation technique of FIG. 3. FIG. 4 summarizes a technique wherein calibration is performed based on calibration values obtained within the particular patient in which the pacer/ICD is implanted. That is, the conversion values are optimized for use with the particular patient. The procedure of FIG. 4 is performed by a physician during the implant procedure of the pacer/ICD while venous access is readily available and a Swan-Ganz catheter can be easily inserted. The procedure in FIG. 4 may be repeated or performed alternatively at a follow-up session sometime after implantation of the pacer/ICD following the acute post-implant phase during which the implanted leads undergo healing process that is known to affect the measured impedance signals. At step 210, an external calibration system (such as the external programmer of FIG. 21) detects or inputs a first conductance calibration value ($G_1$) and a corresponding first LAP calibration value ($LAP_1$) measured while the patient is at rest. Preferably, the conductance value is detected by the pacer/ICD itself using its leads and its internal detection circuitry, then transmitted to the external system. Simultaneously, $LAP_1$ is detected using, e.g., a Swan-Ganz catheter to measure PCWP. The LAP value is also relayed to the external programmer.

At step 212, detects or input a second conductance calibration value ($G_2$) and a corresponding second LAP calibration value ($LAP_2$) measured at a time when the patient is subject to a condition significantly affecting LAP so that $LAP_2$ differs substantially from $LAP_1$. For example, the physician may have the patient perform isometric muscle contractions, particular using thoracic muscles, so as to change LAP within the patient. Alternatively, the physician may administer vasodilatation or vasoconstriction medications, so as to change LAP, or may temporarily reprogram the pacer/ICD to perform rapid pacing, which also changes LAP. Still further, the physician may have the patient perform the Valsalva maneuver, which reduces effective LAP secondary to reduced venous return. The Valsalva maneuver occurs when a patient forcibly exhales for about 15 seconds against a fixed resistance with a closed glottis while contracting the abdominal muscles. A sudden transient increase in intra-thoracic and intra-abdominal pressures occurs, which tends to empty the chambers of the heart of blood, such that within 1 to 2 seconds (phase I of the Valsalva maneuver) the effective right atrial and right ventricular pressures drop to zero, while following 5 seconds (Late phase II) the effective left atrial and left ventricular pressures tend to reach zero. Again, the conductance value is detected by the pacer/ICD itself then transmitted to the external system. $LAP_2$ is simultaneously detected using the Swan-Ganz catheter. Thus, after step 212, the external system has obtained at least two pairs of calibration values ($LAP_1$, $G_1$ and $LAP_2$, $G_2$) where the LAP values differ substantially from one another. Since conductance through the left atrium varies due to changes in left atrial blood volume that correspond to changes in the LAP, the conductance values likewise differ from one another, permitting reliable calculation of the slope and baseline values.

At step 214, the external system calculates $Slope_G$ using:

$$Slope_G = (LAP_2 - LAP_1)/(G_2 - G_1).$$

At step 216, the external system calculates $Baseline_G$ (also referred to herein as $bLAP_G$) using:

$$Baseline_G = LAP_1 - Slope_G * G_1.$$

These values are then transmitted to the pacer/ICD for storage therein for use in estimating LAP based on newly detected values of impedance using the technique of FIG. 3. Preferably, LAP values provided by the pacer/ICD are compared with LAP values detected using the Swan-Ganz catheter to verify that the estimation system of the pacer/ICD has been properly calibrated.

More generally, the first and second impedance-derived calibration values are also referred to herein as $C_1$ and $C_2$. The external system calculates Slope using:

$$Slope = (LAP_2 - LAP_1)/(C_2 - C_1).$$

The external system calculates Baseline using:

$$Baseline = LAP_1 - Slope * C_1.$$

As will become apparent, the impedance-derived calibration values need not be conductance values, but can be other values derived from impedance, such as cardiogenic pulse amplitude values.

Figure 5:
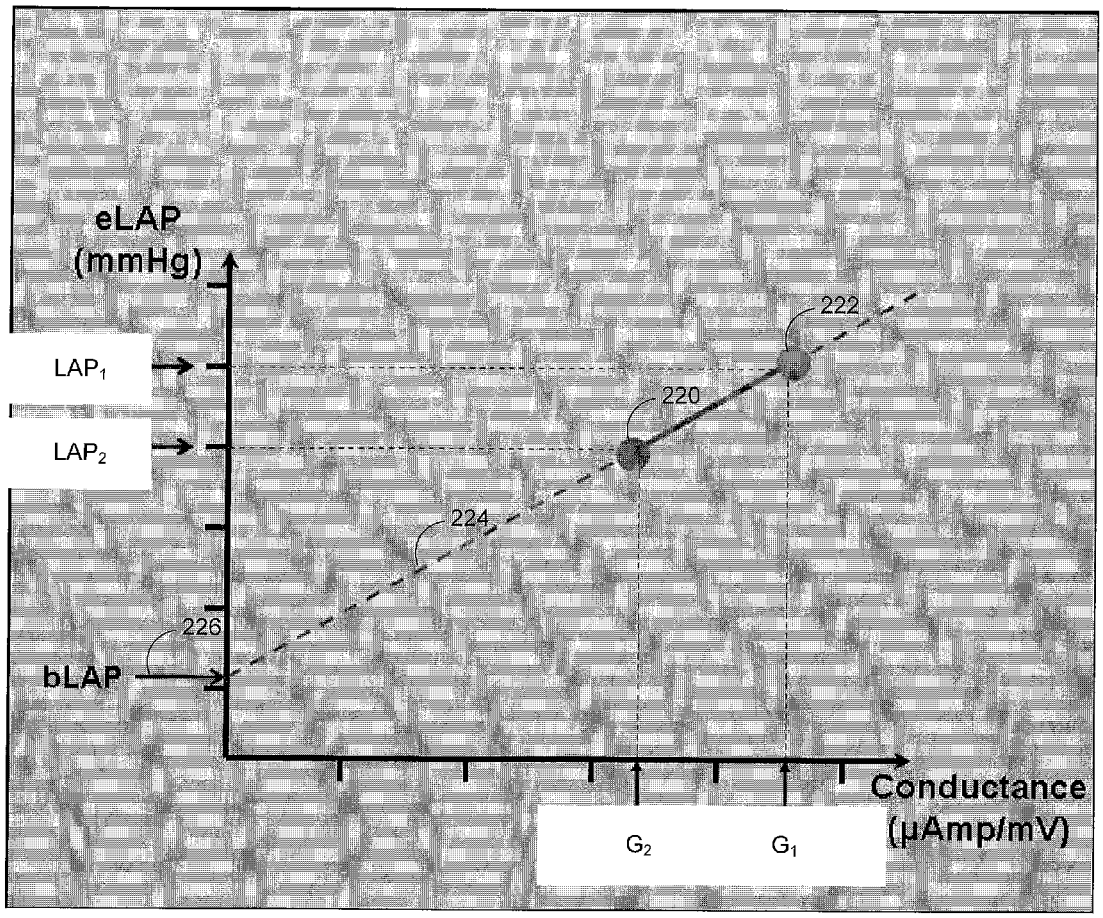
FIG. 5 is a graph illustrating a linear relationship between electrical conductance and LAP calibration parameters exploited by the calibration technique of FIG. 4.

FIG. 5 illustrates an exemplary pair of calibration values 220, 222, along with exemplary slope 224 and baseline (bLAP) values 226 derived therefrom using the technique of FIG. 4. Although only two pairs of calibration values are used in the example of FIG. 4, it should be understood that additional pairs of calibration values may be obtained. Linear regression techniques may be used to derive slope and baseline values from a plurality of pairs of calibration values. Also, as indicated by step 218, the recalibration procedure of FIG. 4 can be repeated periodically (such as during subsequent follow-up sessions with the patient) to update both the slope and baselines values to respond to changes, if any, that may arise within the patient, perhaps due to scarring near the sensing electrodes, which might affect the conductance values. Alternatively, a re-calibration technique may be performed by the pacer/ICD itself that re-calibrates only the baseline value. This is summarized in FIG. 6.

Figure 6:
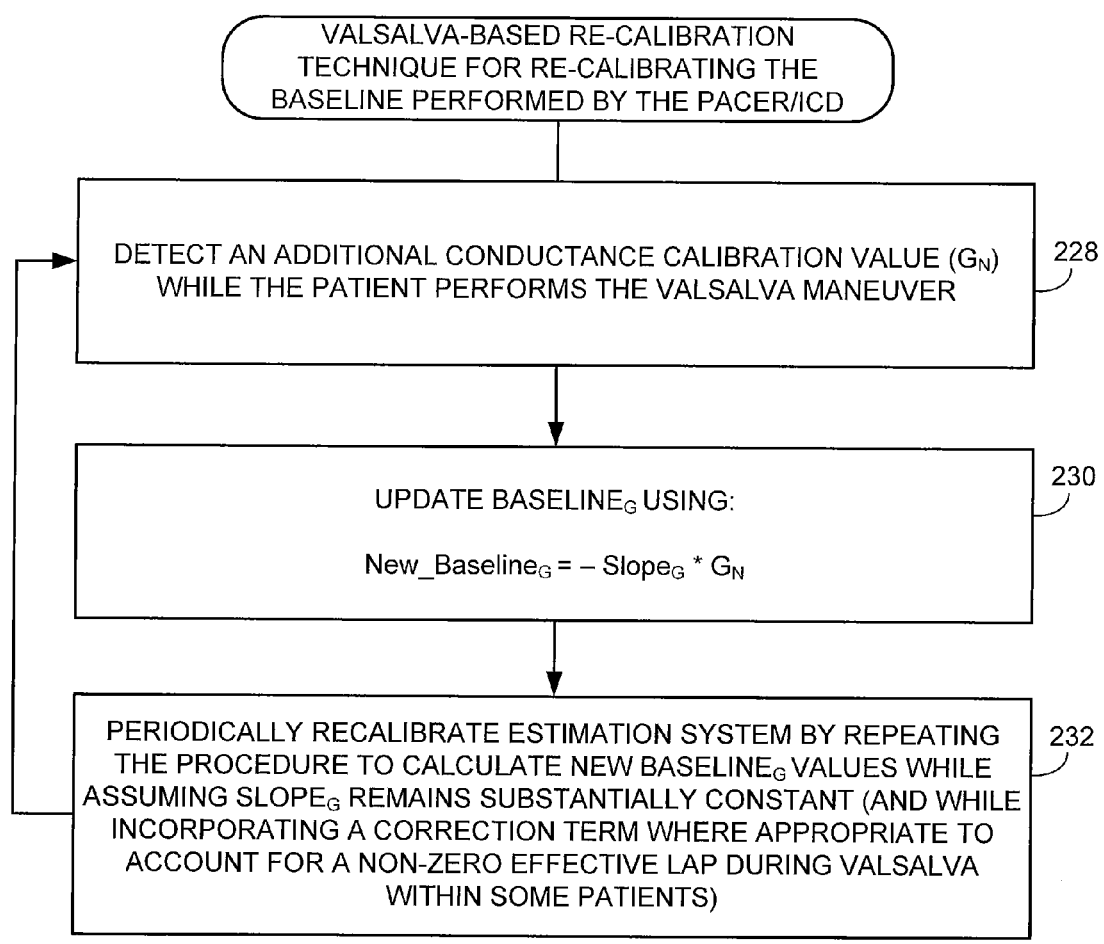
FIG. 6 is a flow diagram illustrating an exemplary procedure for re-calibrating the baseline value of the LAP-based technique of FIG. 3 using additional calibration parameters obtained within the patient in which the system is implanted.

FIG. 6 summarizes a recalibration procedure performed by the pacer/ICD to re-calibrate the baseline value. The procedure exploits the assumption that the slope value, once calculated for a particular patient, typically does not change significantly within the patient. This allows the baseline value to be re-calibrated independently of the slope value. At step 228, the pacer/ICD detects an additional conductance calibration value ($G_N$) while the patient performs the Valsalva maneuver. As already explained, during the Valsalva maneuver effective LAP drops to zero or near zero. Hence, a separate measurement of effective LAP is not required. Under the assumption that effective LAP drops to zero at the time when the additional conductance value ($G_N$) is measured, the baseline value can be re-calculated, at step 230, based on the previous slope and the new conductance value ($G_N$) using:

$$New\_Baseline_G = Slope_G * G_N.$$

A particularly attractive feature of this recalibration procedure is that it is non-invasive and can be performed in the ambulatory setting in the physician's office during a routine follow-up visit. As already noted, if the lungs are "dry" and there is only a change in pulmonary venous volume with emptying during Valsalva, conductance should fall to a new zero baseline value as well. If there is extravascular pulmonary fluid accumulation, and the impedance vector primarily passes through the lung, impedance may not change substantially during Valsalva because overall interstitial lung fluid does not change substantially, only by the fraction of intravascular blood emptying from the pulmonary veins. Preferably, re-calibration is performed while the patient is clinically stable and the lungs are "dry". Also, by using an impedance vector passing through the left atrium, the affect of any interstitial pulmonary fluids on the detected impendence/conductance values is reduced. Still further, within at least some patients, even when using an impedance vector passing through a cardiac chamber, changes in impedance during Valsalva may be somewhat unpredictable because of changing intra-electrode distances and changing fluid volumes. Accordingly, in at least some patients, Valsalva-based re-calibration techniques may not achieve precise re-calibration due to these factors. Within those patients, other re-calibration techniques are preferably used, which do not necessarily exploit Valsalva.

In some patients with diastolic heart failure and poor left ventricular compliance who may have higher cardiac filling pressures (PCWP>20 mmHg) even when well compensated, the effective LAP may not drop completely to zero during a Valsalva maneuver and a correction term may need to be applied to account for this possibility. (See, for example, FIG. 5 of the Eigler, et al. patent application, cited above.) In order to determine whether a particular patient requires such a correction term a third measurement of the conductance ($G_3$) during the original calibration procedure FIG. 4 should be obtained while the patient is performing the Valsalva maneuver. This assumes that $G_1$ and $G_2$ when obtained not during a Valsalva maneuver. The correction term ($eLAP_{VALSALVA}$) is simply computed using:

$$eLAP_{VALSALVA} = G_3 * Slope_G + Baseline_G$$

wherein $eLAP_{VALSALVA}$ is an effective LAP pressure value. Ideally, if the blood volume inside the left atrium significantly decreases during the Valsalva maneuver, then $eLAP_{VALSALVA}$ will be near zero. Step 230 may alternatively be computed using:

$$New\_Baseline_G = eLAP_{VALSALVA} - Slope_G * G_N.$$

The response of intracardiac pressures to the Valsalva is discussed in McClean et al., "Noninvasive calibration of cardiac pressure transducers in patients with heart failure: An aid to implantable hemodynamic monitoring and therapeutic guidance", Journal of Cardiac Failure, Vol. 12 No. 7 2006, pp 568-576. It is described therein that during the Valsalva maneuver the effective PCWP reduces nearly to zero as described above. A similar observation was observed for other chambers of the heart. In particular, the effective residual pressure within a specific cardiac chamber ($P_{eff}$) was computed as the difference between the measured intracardiac pressure ($P_{intracardiac}$) and the simultaneous intrathoracic or airway pressure ($P_{airway}$) averaged over the time interval from 5 to 10 seconds after the initiation of the Valsalva maneuver (Late phase II). The effective intracardiac pressure ($P_{eff}$) is computed using:

$$P_{eff} = P_{intracardiac} - P_{airway}$$

where ($P_{airway}$) is detected, e.g., using an external pressure detection system. See, for example, the upper airway apparatus of FIG. 2 of U.S. Patent Application 2004/0019285 of Eigler, et al., entitled "Apparatus for Minimally Invasive Calibration of Implanted Pressure Transducers", which is incorporated by reference herein in its entirety. Thus, in order to estimate the effective LAP ($LAP_{eff}$) during the Valsalva maneuver one may obtain this measurement directly by computing average of the difference between the PCWP and the simultaneous airway pressure over the interval from 5 to 10 seconds following the initiation of the Valsalva maneuver (late Phase II). This may be written more specifically as:

$$LAP_{eff} = PCWP - P_{airway}$$

and $LAP_{eff}$ may be used alternatively as the correction term described above.

The new baseline value is then used when converting additional conductance values to effective eLAP values (step 206 of FIG. 3.) As indicated by step 232, the pacer/ICD can periodically recalibrate its estimation system by repeating the procedure to calculate new $Baseline_G$ values while assuming $Slope_G$ remains substantially constant and using the correction term where appropriate.

In practice, the procedure of FIG. 6 may be initiated by periodically having the pacer/ICD transmit a signal to the bedside monitor providing instructions to the patient to perform the Valsalva maneuver. The pacer/ICD detects the new conductance value during the Valsalva maneuver and updates the baseline value. The pacer/ICD may be additionally programmed to verify that the patient actually performed the Valsalva maneuver by, e.g., analyzing changes in respiration (as detected using otherwise conventional respiration detection techniques) to verify that respiratory patterns consistent with the Valsalva maneuver occur. The pacer/ICD can also time its detection of the additional conductance value based on the respiratory signals to help ensure that the new conductance value is measured at a point when effective LAP is expected to be zero. Alternatively, the re-calibration technique may be performed only under the supervision of a physician or other clinician during a follow-up session with the patient. Still, the re-calibration procedure eliminates the need to directly measure effective LAP during the follow-up using a Swan-Ganz catheter. The catheter is only employed during the original calibration procedure. Thus, FIG. 6 illustrates a technique wherein the baseline value is re-calibrated by the pacer/ICD under the assumption that slope does not change by exploiting the Valsalva maneuver. The Valsalva maneuver may also be exploited to re-calibrate both slope and baseline, if needed within a particular patient. This is illustrated in FIGS. 7 and 8.

Figure 7:
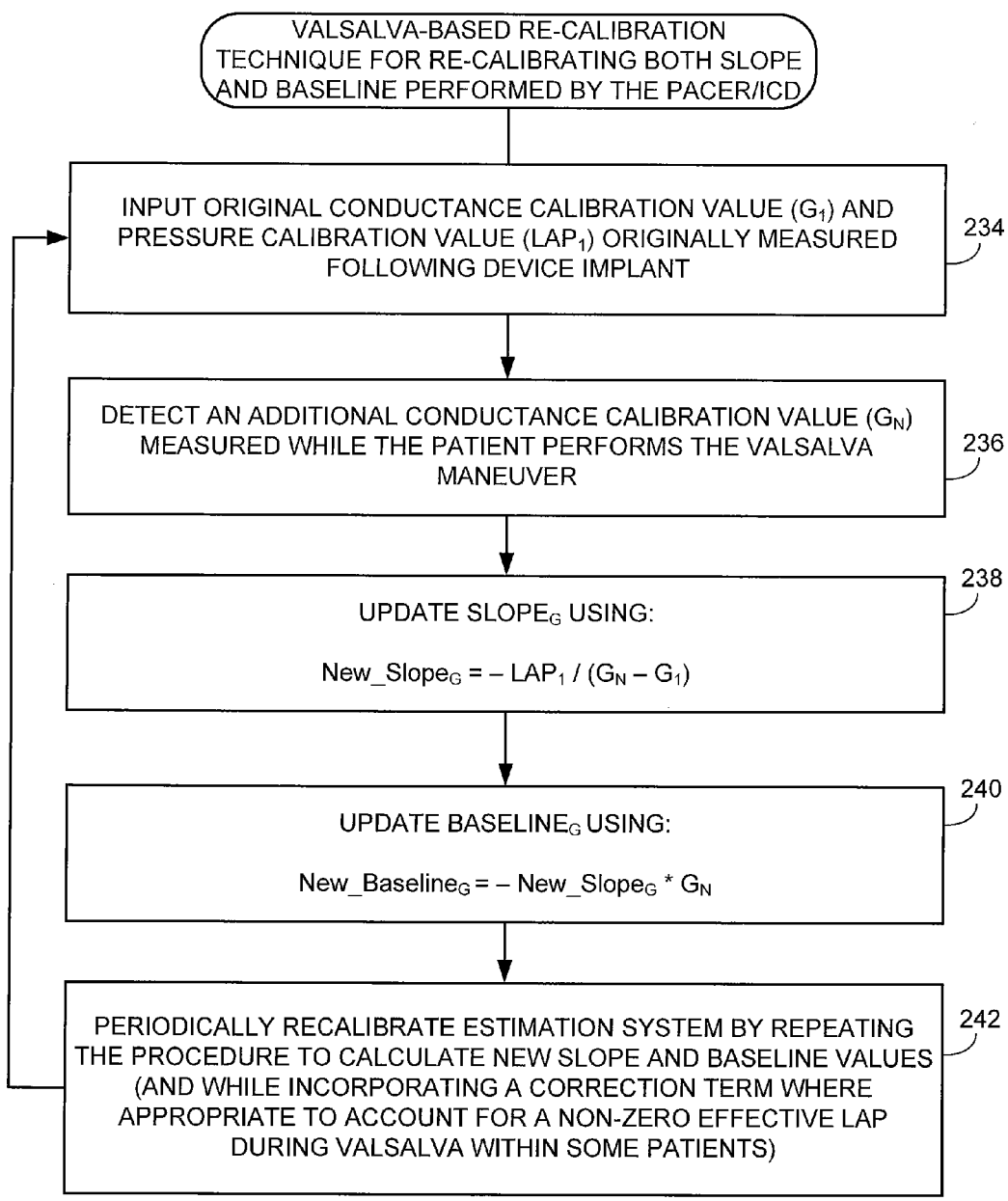
FIG. 7 is a flow diagram illustrating an exemplary procedure for re-calibrating both slope and baseline values of the LAP-based technique of FIG. 3 using additional calibration parameters obtained within the patient in which the system is implanted.
Figure 8:
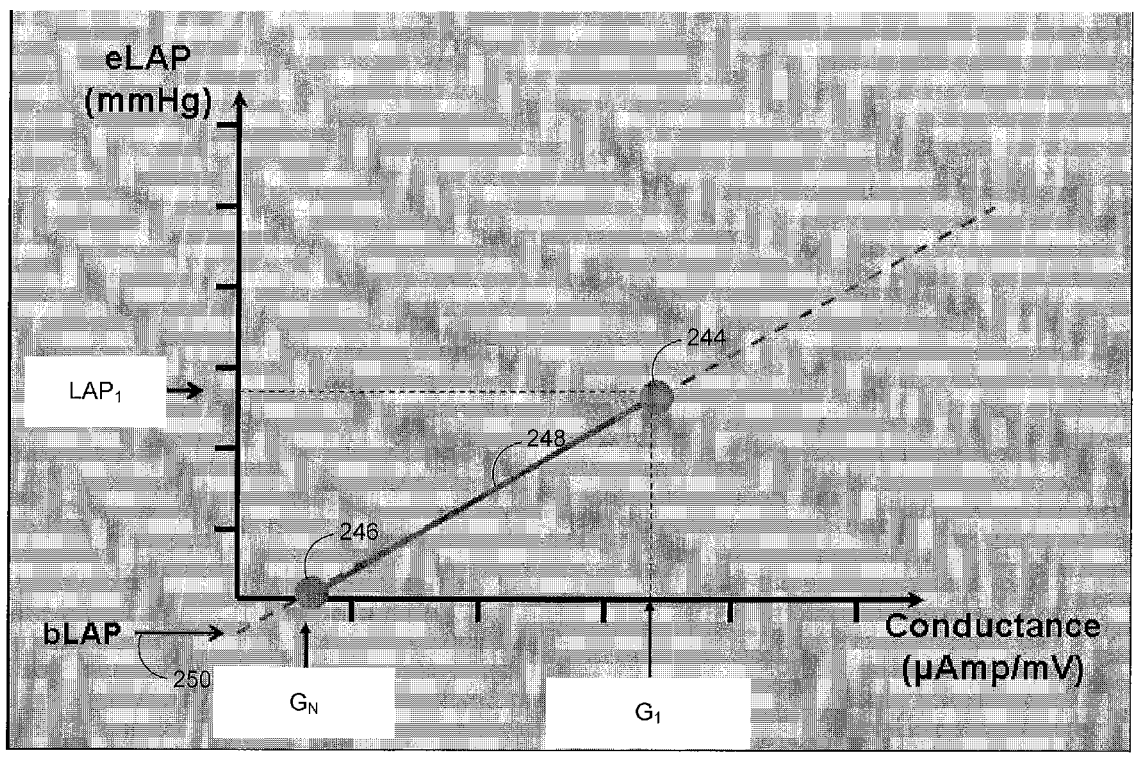
FIG. 8 is a graph illustrating a linear relationship between electrical conductance and LAP calibration parameters exploited by the re-calibration technique of FIG. 7 and, in particular, illustrating a zero LAP value obtained within the patient during the Valsalva maneuver.

FIG. 7 summarizes a recalibration procedure performed by the pacer/ICD to re-calibrate both the slope and baseline values. The procedure can be used in patients where the slope value changes. At step 234, the pacer/ICD inputs the original conductance calibration value ($G_1$) and effective pressure calibration value ($LAP_1$) originally measured following device implant (FIG. 4) or during a previous calibration procedure. At step 236, the pacer/ICD detects an additional conductance calibration value ($G_N$) while the patient performs the Valsalva maneuver. As already noted, during the Valsalva maneuver effective LAP typically drops to at or near zero and so separate measurement of effective LAP is not required. Rather, it is assumed that effective LAP is zero when the additional conductance value ($G_N$) is measured, thus allowing the slope to be re-calculated, at step 238, using:

$$\text{New\_Slope}_G = LAP_1 / (G_N - G_1).$$

Once the new slope value is calculated, the new baseline value can be calculated, at step 240, using:

$$\text{New\_Baseline}_G = -\text{New\_Slope}_G * G_N.$$

The new slope and baseline values are then used when converting additional conductance values to effective eLAP values (step 206 of FIG. 3.) As indicated by step 242, the pacer/ICD can periodically recalibrate its estimation system by repeating the procedure to calculate new $\text{Baseline}_G$ and $\text{Slope}_G$ values and using the correction term where appropriate. As with the procedure of FIG. 6, the procedure of FIG. 7 may be initiated by periodically having the pacer/ICD transmit a signal to the bedside monitor providing instructions to the patient to perform the Valsalva maneuver or the procedure may be performed under the supervision of a physician or other clinician.

FIG. 8 illustrates an exemplary pair of calibration values 244, 246, along with exemplary slope 248 and baseline (bLAP) values 250 derived therefrom using the technique of FIG. 7. The first pair of calibration values 244 is obtained following implant. The second pair of calibration values 246 is obtained during the re-calibration procedure while the patient performs the Valsalva maneuver. Since the Valsalva maneuver is being performed, the effective LAP value of the second pair of calibration values 246 is zero and so the pressure need not be measured. The conductance value of the second pair along with the pressure and conductance values of the first pair are used to calculate the new slope 244 and baseline (bLAP) values 250 using the equations of FIG. 7.

Figure 9:
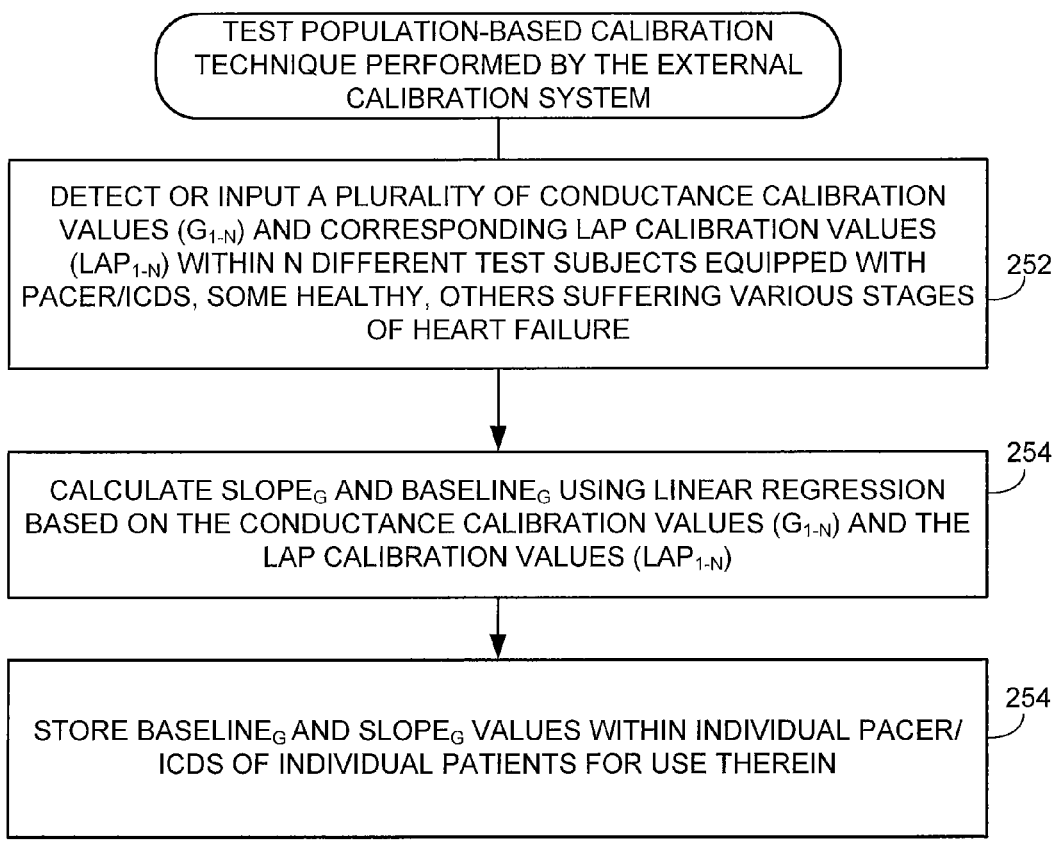
FIG. 9 is a flow diagram illustrating an exemplary procedure for calibrating the LAP-based technique of FIG. 3 using calibration parameters obtained from a population of test subjects.
Figure 10:
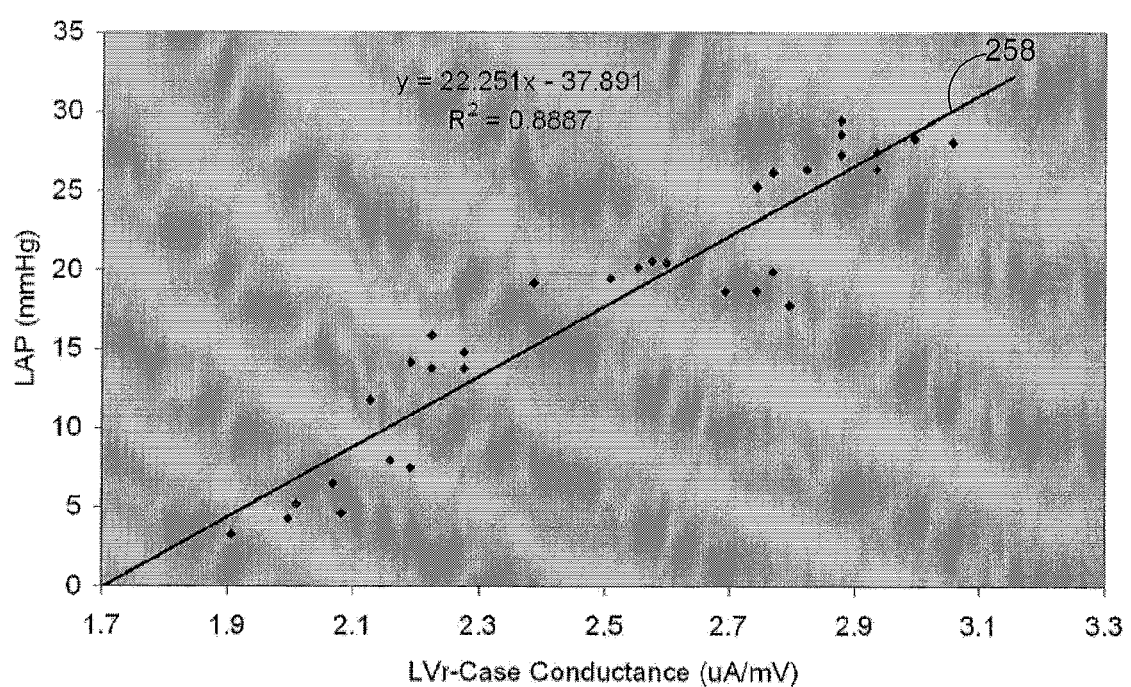
FIG. 10 is a graph illustrating a linear correlation between LAP and electrical conductance that may be exploited by the calibration procedures of FIG. 9.

Turning now to FIGS. 9 and 10, linear regression techniques for calibrating or re-calibrating the conductance-based estimation procedure will be summarized. These techniques exploit a plurality of values for determining the slope and baseline values. In the specific example of FIG. 9, data is obtained from a plurality of test patients subject to various stages of heart failure and have various LAP values. Beginning at step 252, the external calibration system detects or inputs a plurality of conductance calibration values ($G_{1-N}$) and corresponding LAP calibration values ($LAP_{1-N}$) within N different test subjects equipped with pacer/ICDs, some healthy, others suffering differing stages of heart failure, i.e. differing levels of severity of heart failure. The conductance values are detected by the pacer/ICDs of the test subjects, then relayed to the external calibration system. The LAP values may be obtained using Swan-Ganz catheters or the like. Since the test subjects exhibit differing stages of heart failure, differing values of LAP are thereby exhibited. At step 254, the external system then calculates $\text{Slope}_G$ and $\text{Baseline}_G$ values using linear regression based on the conductance calibration values ($G_{1-N}$) and the LAP calibration values ($LAP_{1-N}$). At step 256, the external system then stores the $\text{Slope}_G$ and $\text{Baseline}_G$ values within individual pacer/ICDs of individual patients for use therein. By obtaining data from a population of test subjects, the slope and baseline values are therefore likely to be effective within a wide range of patients. In some patients, these values may be sufficient to provide an adequate estimate of LAP. In other patients, these values may be used as starting points for further re-calibration. For example, the slope value obtained via the technique of FIG. 9 may be used within a wide range of patients along with patient-specific baseline values obtained using the baseline-only re-calibration procedure of FIG. 6.

FIG. 10 illustrates a range of LAP and conductance values from which a slope value 258 is obtained via linear regression. The actual data of FIG. 10 was obtained from a single (animal) test subject in which heart failure was induced via a rapid pacing protocol. However, a similar distribution of LAP and conductance values is exhibited within human patients as well, when heart failure occurs naturally.

Thus, FIGS. 3-10 illustrate various conductance-based LAP estimation techniques. Turning now to FIGS. 11-16, various alternative embodiments will be described wherein parameters other than conductance are exploited. Some of the steps of these alternative procedures are similar to steps already described and hence will be described again in detail.

Figure 11:
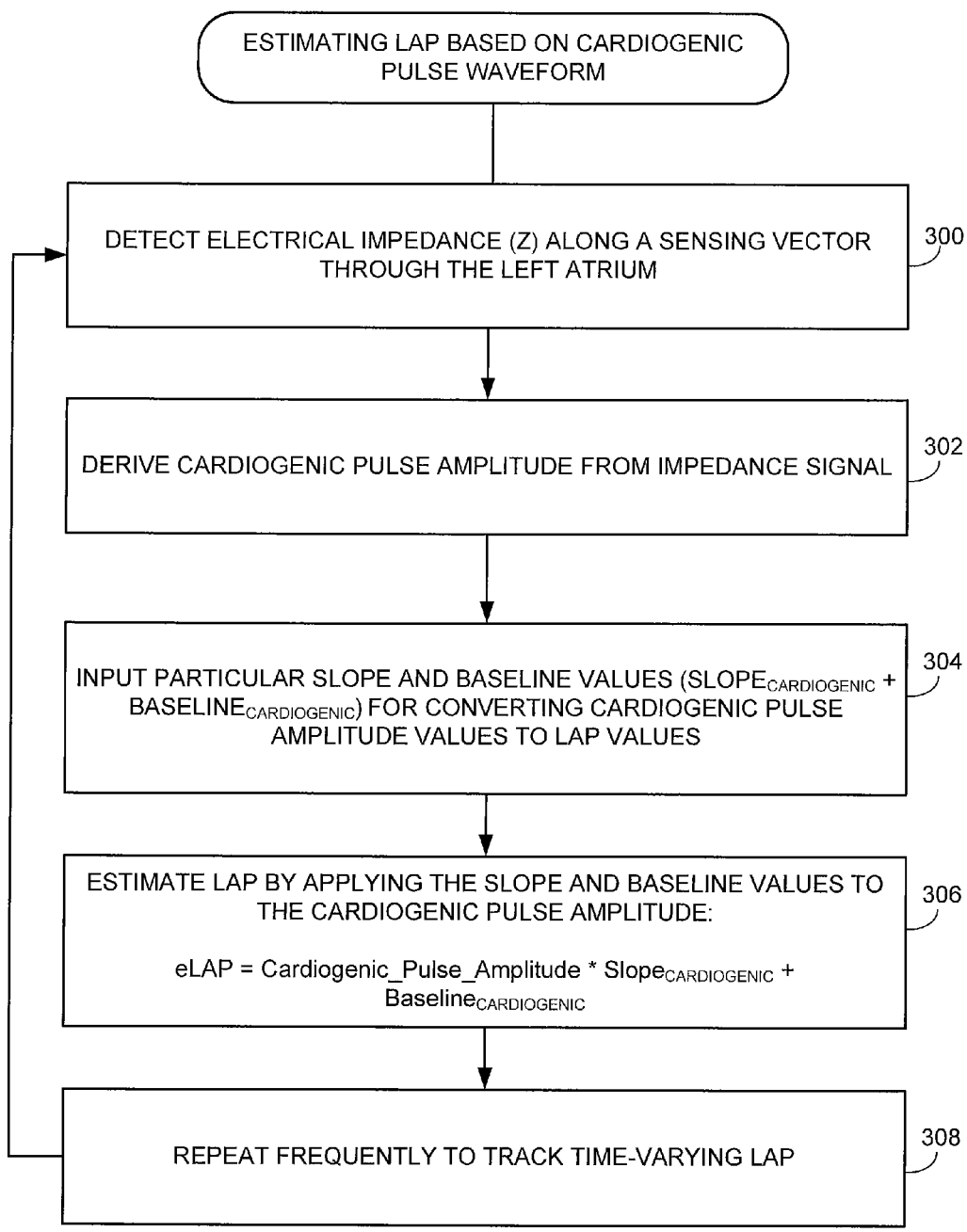
FIG. 11 is a flow diagram summarizing a second illustrative technique wherein LAP is estimated based on cardiogenic pulse amplitudes, and which also may be performed in accordance with the general technique of FIG. 2.

FIG. 11 illustrates a cardiogenic pulse amplitude-based LAP detection example. That is, the parameter derived from the electrical impedance signal (Z) (particularly $Z_0$) at step 102 of FIG. 2 is cardiogenic pulse amplitude. Alternatively, the cardiogenic pulse amplitude may be obtained without necessarily first detecting impedance by, for example, detecting conductance instead. Continuing with an impedance-based, with this technique, it is assumed that cardiogenic pulse amplitude is inversely proportional to LAP (at least when the cardiogenic pulse amplitude is derived from an impedance signal sensed along a vector passing through the left atrium.) Accordingly, a linear model relating cardiogenic pulse amplitude to LAP is exploited. At step 300, the pacer/ICD detects electrical impedance (Z) along a sensing vector through the left atrium. At step 302, the pacer/ICD derives a cardiogenic pulse amplitude from the waveform of the detected electrical impedance signal. At step 304, the pacer/ICD inputs the particular slope and baseline values ($\text{Slope}_{CARDIOGENIC} + \text{Baseline}_{CARDIOGENIC}$) for converting cardiogenic pulse amplitudes to LAP, which are predetermined conversion values that the pacer/ICD retrieves from memory. Calibration techniques of the type discussed above may be used to initially derive the conversion values and to re-calibrate the values, if needed. At step 306, the pacer/ICD estimates LAP by applying the slope and baseline values (input at step 304) to the cardiogenic pulse amplitude value (derived at step 302):

$$eLAP = \text{Cardiogenic\_Pulse\_Ampltide} * \text{Slope}_{CARDIOGENIC} + \text{Baseline}_{CARDIOGENIC}$$

As indicated by step 308, the pacer/ICD can repeat steps 300-306 frequently so as to track a time-varying LAP function, i.e. LAP(t), based on cardiogenic pulse amplitude values. That is, in some implementations, individual cardiogenic pulse amplitude values are detected substantially in real-time so as to permit changes in LAP to be tracked substantially in real-time as well. LAP estimates determined from conductance values may be combined with LAP estimates determined from the cardiogenic pulse amplitudes to provide a combined LAP estimate.

Figure 12:
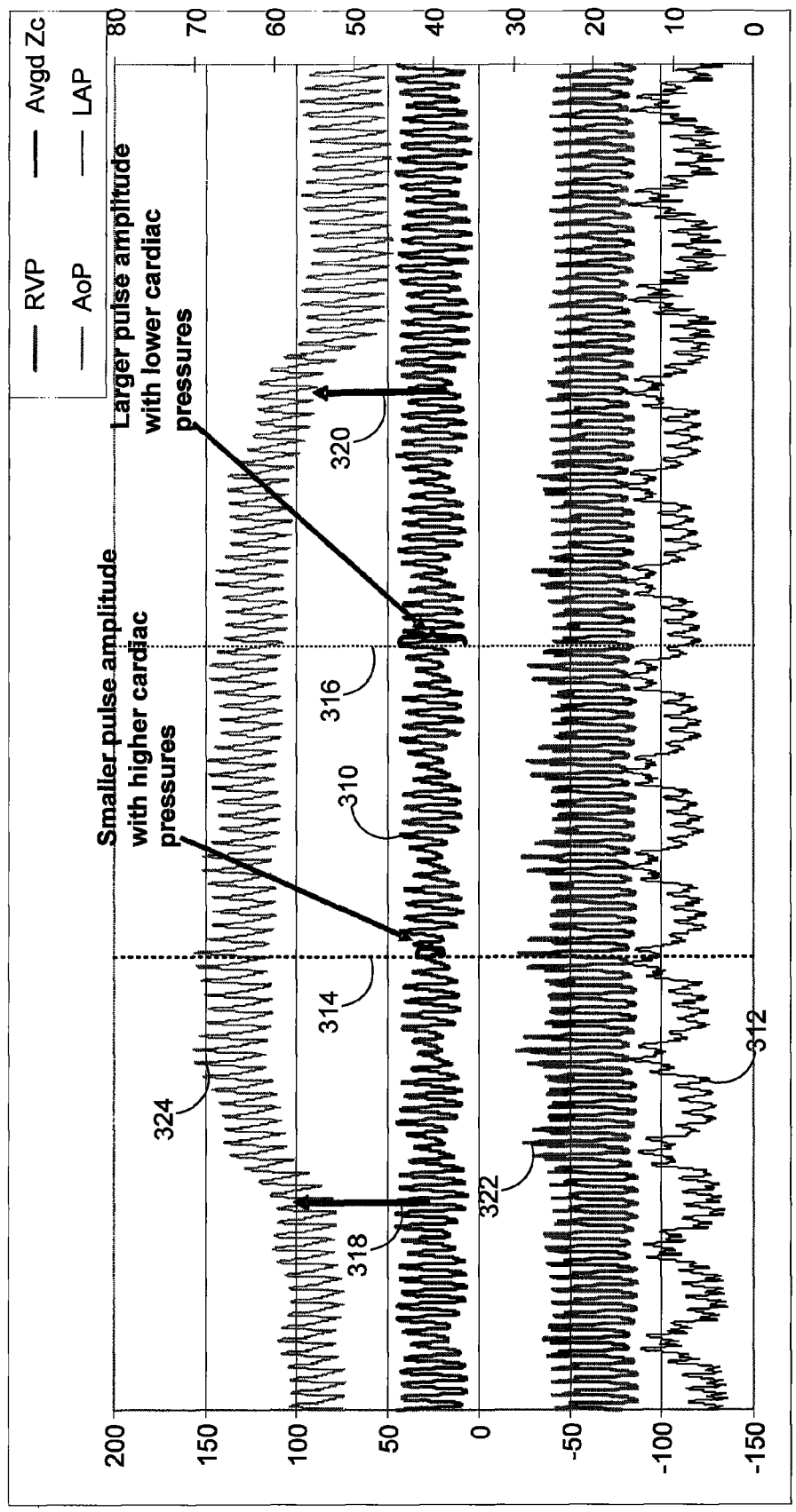
FIG. 12 is a graph illustrating cardiogenic pulse amplitude and LAP that may be exploited by the calibration procedures of FIG. 9.

FIG. 12 illustrates cardiogenic pulse amplitudes. Briefly, the figure includes graphs of data obtained for an animal test subject including a cardiogenic impedance signal trace 310 and a corresponding LAP trace 312. Note that, at times when the cardiogenic pulse amplitude is low, such as at time 314, LAP is large. Likewise, at times when the cardiogenic pulse amplitude is large, such as at time 316, LAP is small. That is, the two signals are substantially inversely proportional to each other. In the example of FIG. 12, a pressure afterload was induced within the animal using a balloon beginning at time 318 and ending at time 320 to emulate heart failure. It can also be seen that the magnitude of the difference between small pulse amplitudes and large pulse amplitude is greater during the emulated heart failure, suggesting that cardiogenic pulse amplitude-based LAP estimation technique is particularly effective in patients with heart failure. For comparison purposes, the figure also provides traces for right ventricular pressure (RVP) 322 and aortic pressure (AoP) 324. Aortic pressure increased significantly due to balloon inflation. Note that the horizontal time scale of the figure covers approximately one minute.

Figure 13:
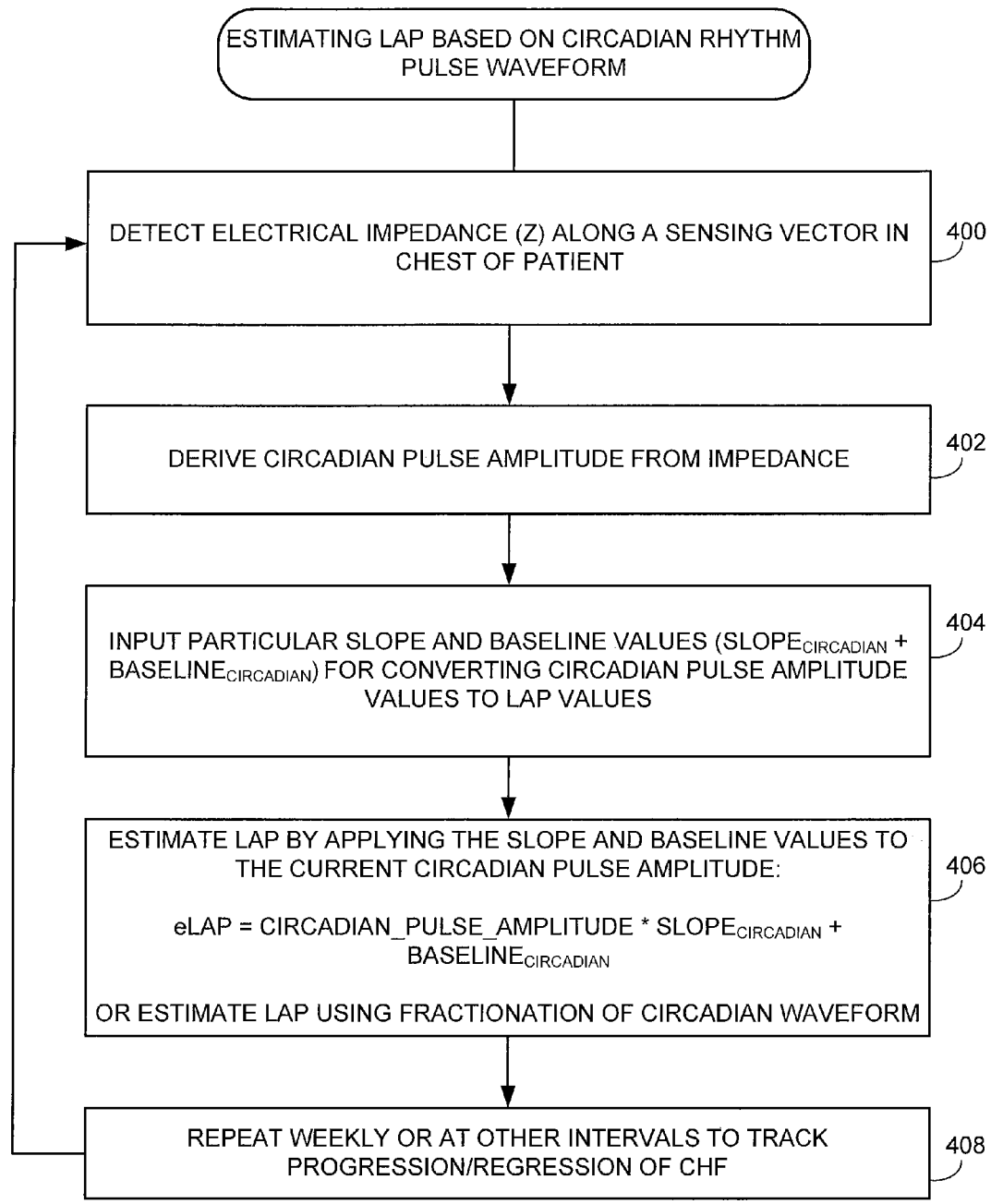
FIG. 13 is a flow diagram summarizing a third illustrative technique wherein LAP is estimated based on circadian rhythm pulse amplitudes, and which also may be performed in accordance with the general technique of FIG. 2.

FIG. 13 illustrates a circadian pulse amplitude-based LAP detection example. That is, the parameter derived from the electrical impedance signal (Z) at step 102 of FIG. 2 is the circadian pulse amplitude value (and is typically derived from the raw impedance signal ($Z_0$)). Alternatively, the circadian pulse amplitude may be obtained without necessarily first detecting impedance by, for example, detecting conductance instead. Continuing with an impedance-based, as already noted, the circadian pulse amplitude represents the daily variation in the impedance signal and is preferably calculated once per day. Within healthy patients, there is typically a significant daily variation in circadian impedance and so the circadian pulse amplitude may be 20 ohms or more. Within patients suffering from heart failure, however, there is typically little or no significant daily variation in circadian impedance and so the circadian pulse amplitude is at or near zero. Hence, progression of heart failure correlates with a decrease in circadian pulse amplitudes. There is also a correlation with LAP and heart failure, i.e. LAP increases due to progression of heart failure. Accordingly, there is a correlation between decreasing circadian pulse amplitudes and increasing LAP. With the technique of FIG. 14, it is assumed that circadian pulse amplitude is inversely proportional to LAP. Accordingly, a linear model relating circadian pulse amplitude to LAP is exploited.

At step 400, the pacer/ICD detects impedance along a sensing vector in the chest of the patient, such as between an LV tip electrode and the device housing. The sensing vector need not pass through the left atrium. At step 402, the pacer/ICD derives a circadian pulse amplitude from the impedance signal. The circadian component of the electrical impedance signals is the component that does not vary due to respiration or the beating of the heart of the patient. It remains substantially constant, except for the aforementioned circadian variations. The circadian pulse amplitude represents the difference between impedance waveform amplitudes at night and those during the day and is preferably calculated once per day. Circadian pulse amplitudes are illustrated in FIG. 14.

Figure 14:
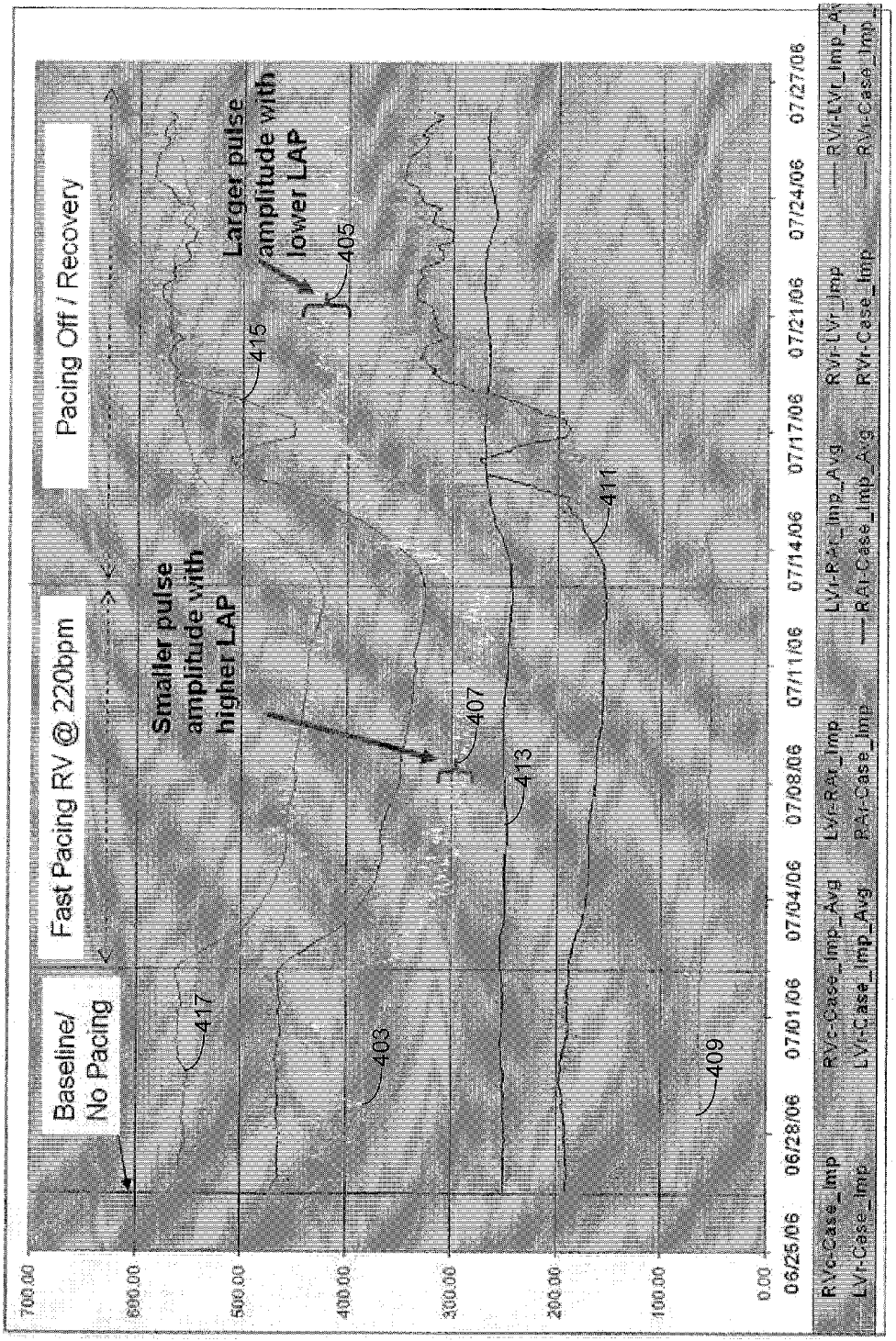
FIG. 14 includes a graph illustrating circadian variations in electrical impedance values from which the circadian pulse amplitude of FIG. 13 is derived.

FIG. 14 illustrates a circadian impedance signal 403 tracked over a one month period within an animal test subject in which heart failure is emulated via rapid pacing during a middle portion of the time interval shown. Circadian variations in signal 403 are exhibited. These are most clearly seen in the portions of the graph wherein rapid pacing is not performed, i.e. during the early and later portions of the data shown. The circadian pulse amplitude represents the difference between peak and nadir points within the circadian impedance signal over a one-day period. Reference numeral 405 identifies a relatively large circadian pulse amplitude occurring during a period of time when heart failure is not being emulated, and hence LAP is high. Reference numeral 407 identifies a relatively smaller circadian pulse amplitude occurring during a period of time when heart failure is being emulated, and hence LAP is lower. (LAP itself is not shown in the figure.) Although the data of FIG. 14 was obtained from a single (animal) test subject in which heart failure was temporarily emulated via a rapid pacing protocol, a similar variation in circadian pulse amplitude is exhibited within human patients as well, when heart failure occurs naturally. For comparison purposes, the figure also provides traces for $RV_{coil}$-case impedance/average impedance 409, $RV_{ring}$-case impedance/average impedance 411, $RA_{ring}$-case impedance/average impedance 413, $RV_{ring}$-$LV_{ring}$ impedance/average impedance 415, and $LV_{ring}$-$RA_{ring}$ impedance/average impedance 417, which demonstrate that not all vectors are equal in their ability to detect the circadian pulse amplitude. This may require individualizing the selected vector for estimating LAP in the clinical setting.

At step 404 of FIG. 13, the pacer/ICD inputs the particular slope and baseline values ($Slope_{CIRCADIAN}$, $Baseline_{CIRCADIAN}$) for converting circadian pulse amplitudes to LAP, which are predetermined conversion values that the pacer/ICD retrieves from memory. The conversion values may be obtained from a population of test subjects using linear regression techniques, as with the calibration technique of FIG. 9. At step 406, the pacer/ICD estimates LAP by applying the slope and baseline values (input at step 404) to the circadian pulse amplitude value (derived at step 402):

$$eLAP = Circadian\_Pulse\_Amplitde * Slope_{CIRCADIAN} + Baseline_{CIRCADIAN}$$

By way of a simple example, the circadian pulse amplitude within a healthy patient may be 20 ohms with an LAP of 10 mmHg. Within a patient with severe CHF, the circadian pulse amplitude may be 0 ohms with an LAP of 30 mmHg. Accordingly, the pacer/ICD can estimate LAP for a particular patient by scaling the circadian pulse amplitude value detected therein. That is, if the circadian pulse amplitude is found to be 10 ohms within the patient, the pacer/ICD then estimates the LAP of the patient as being 20 mmHg. As indicated by step 408, the pacer/ICD can repeat steps 400-406 once per day so as to track changes in LAP occurring over extended intervals (i.e. weeks or months). That is, unlike the implementations described above, changes in LAP are not tracked in real-time when using circadian pulse amplitudes.

Referring again to FIG. 14, note that during the period of time while heart failure is emulated the circadian waveform is quite "noisy", i.e. there is a relatively high degree of fractionation. This period of increased fractionation is also correlated with increased LAP. The fractionation of the circadian waveform may also be used to estimate LAP. Fractionation is more fully described in the following section, specifically with regard to the fractionation of the cardiogenic component of the impedance signal. Techniques for exploiting the fractionation of the cardiogenic impedance waveform are described for use in estimated LAP. These techniques may also be applied to estimating LAP based on fractionation of the circadian impedance waveform.

Figure 15:
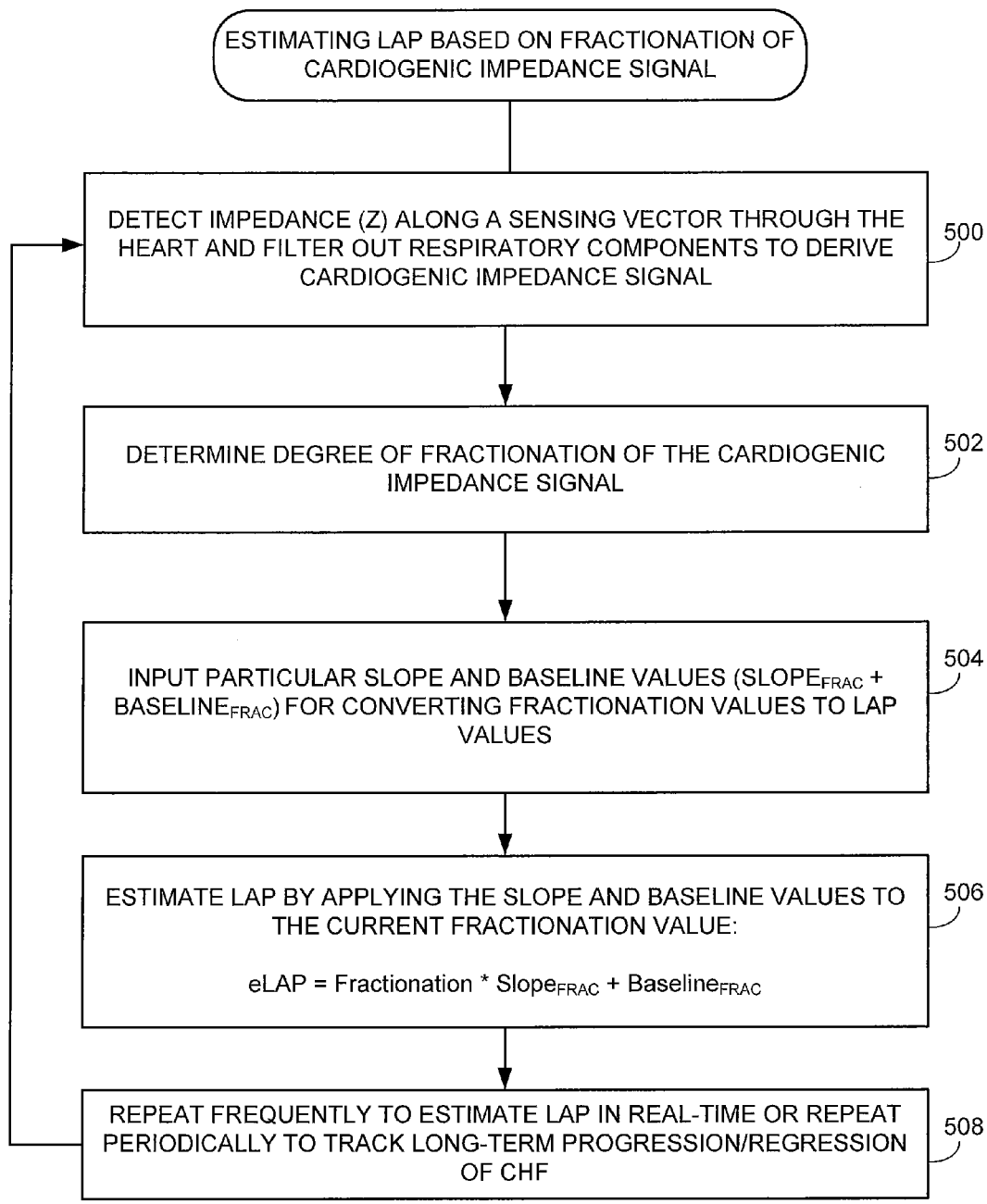
FIG. 15 is a flow diagram summarizing a fourth illustrative technique wherein LAP is estimated based on fractionation of cardiogenic impedance signals, and which also may be performed in accordance with the general technique of FIG. 2.
Figure 16:
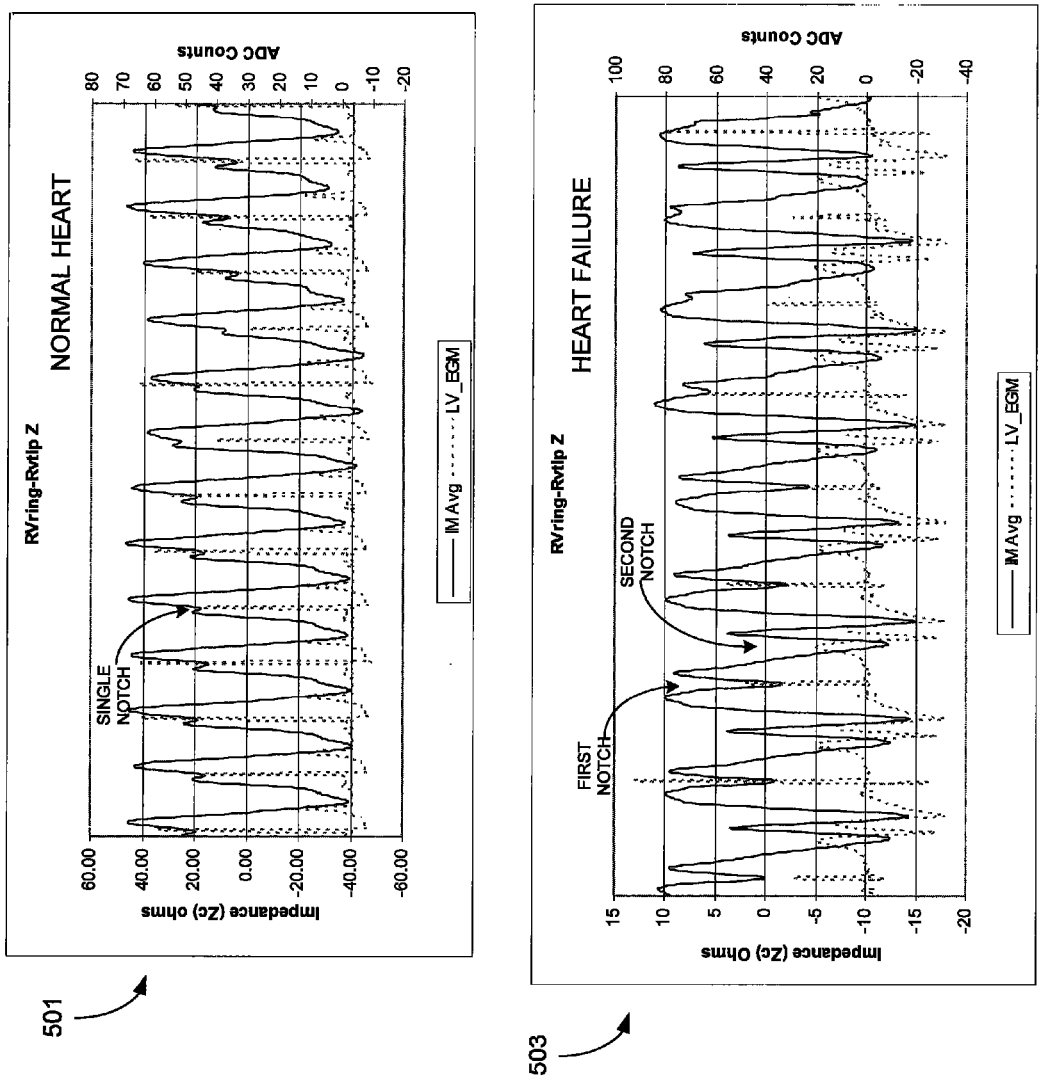
FIG. 16 is a graph illustrating exemplary cardiogenic impedance signals that may be processed in accordance with the technique of FIG. 15, and particularly illustrating the fractionation of the cardiogenic impedance signal exhibited during heart failure emulated in an animal test subject.

FIG. 15 illustrates a fractionation-based LAP detection example. That is, the parameter derived from the electrical impedance signal (Z) (preferably from the cardiogenic impedance signal ($Z_0$)) at step 102 of FIG. 2 is an indication of the fractionation of cardiogenic components of the impedance signal. Alternatively, the fractionation value may be obtained without necessarily first detecting impedance by, for example, detecting conductance instead. Continuing with an impedance-based example, as already noted, fractionation represents the degree of fractionation in a cardiogenic component of the impedance signal, i.e. that portion of the impedance signal that varies in accordance with the beating of the heart. The cardiogenic component of the impedance signal may be derived from the detected impedance signal by filtering out non-cardiogenic components using otherwise conventional techniques. Fractionation increases due to increasing mechanical dyssynchrony and abnormal transvalvular flow patterns within the heart arising due to heart failure. LAP also typically increases due to heart failure. Accordingly, there is a correlation between increasing fractionation and increasing LAP. With the technique of FIG. 14, it is assumed that increasing fractionation of the cardiogenic component of the impedance signal is directly proportional to LAP. Accordingly, LAP may be estimated based on fractionation using conversion factors calibrated for converting fractionation values to LAP values.

At step 500, the pacer/ICD detects electrical impedance along a sensing vector passing through the heart of the patient and filters out non-cardiogenic components. However, the sensing vector need not pass through the left atrium. At step 502, the pacer/ICD determines the degree of fractionation of the cardiogenic impedance signal. Fractionation of a cardiogenic impedance signal due to heart failure is illustrated with FIG. 16. A first graph 501 illustrates a cardiogenic impedance trace (solid line) and an IEGM trace (dotted line) for a patient without significant heart failure. The impedance trace (IM avg) was obtained via bipolar sensing RV tip to RV ring. The IEGM in an LV IEGM and is shown scaled according to "counts" from an analog to digital converter (ADC). A second graph 503 instead illustrates a cardiogenic impedance trace (solid line) and an IEGM trace (dotted line) for a patient with heart failure. As can be seen, within the normal heart trace 501, the portion of the cardiogenic impedance signal associated with each individual heart beat exhibits one notch. This single notch is arises due to the uniform contraction of the RV and the LV and corresponds to the QRS complex of the IEGM. However, in the diseased heart of graph 503, an additional significant notch appears within the cardiogenic impedance trace within the time interval of the T-wave of the IEGM. This additional notch appears to occur due to a time delay between LV contraction and RV contraction and hence is indicative of mechanical dyssynchrony between the LV and RV associated with heart failure.

When determining the degree of fractionation of the cardiogenic impedance signal at step 502 of FIG. 15, the pacer may calculate a fractionation index representative of a degree of fractionation of the cardiogenic impedance signal. The fractionation index may be derived, e.g., by simply counting a number of notches appearing within portions of the signal representative of individual heartbeats. A patient whose heartbeat exhibits five notches has a higher degree of fractionation than a patient whose heartbeat exhibits only four notches. As noted, the notches often correspond to periods of time when chambers of the heart are not beating uniformly, i.e. the greater the number of notches, the greater the degree of mechanical dyssynchrony. Though, even a healthy and fully synchronized heart will exhibit some notches within the cardiogenic impedance signals. That is, for a normal patient free of heart failure, the characteristic morphology of a cardiogenic impedance pattern for a single heartbeat shows relatively smooth waves that follow the cardiac cycle, with relatively little raggedness (i.e., "fractionation") at the crest of each impedance peak (or trough). During early onset of heart failure, the cardiogenic impedance pattern for a single heartbeat develops a characteristic morphology of notches in or near the crests—i.e., a moderate degree of fractionation. During late heart failure conditions, cardiogenic impedance pattern for a single heartbeat develops a characteristic morphology of high volatility and fractionation, where the magnitude of the notches increases significantly and their frequency of occurrence is high. The fractionation index may also be derived by determining the frequencies associated with the cardiogenic impedance signal using, for example, a Fast Fourier Transform (FFT). The greater the number of notches and troughs within the cardiogenic impedance signal, the higher the frequencies of the signal, and the greater the mechanical dyssynchrony. Techniques for identifying and comparing notches and troughs within a cardiogenic impedance signal are discussed in the related patents, cited above.

At step 504 of FIG. 15, the pacer/ICD inputs the particular slope and baseline values ($Slope_{FRAC}$+$Baseline_{FRAC}$) for converting fractionation values to LAP, which are predetermined conversion values that the pacer/ICD retrieves from memory. The conversion values may be obtained from a population of test subjects using linear regression techniques, as with the calibration technique of FIG. 9. At step 506, the pacer/ICD estimates LAP by applying the slope and baseline values (input at step 504) to the fractionation values (derived at step 502):

$$eLAP=Fractionation*Slope_{FRAC}+Baseline_{CIRCADIAN}$$

By way of a simple example, the cardiogenic impedance signal of a healthy patient may exhibit a single notch with an LAP of 10 mmHg. Within a patient with severe CHF, the cardiogenic impedance signal may exhibit five notches with an LAP of 30 mmHg. Accordingly, the pacer/ICD can estimate LAP for a particular patient by scaling the number of notches detected within the cardiogenic impedance signal of the patient. That is, if three notches are found within the patient, the pacer/ICD then estimates the LAP of the patient as being 20 mmHg. As indicated by step 508, the pacer/ICD can repeat steps 500-506 once per week so as to track changes in LAP occurring over extended intervals (i.e. weeks or months). Alternatively, the estimated LAP derived from fractionation may be obtained in real-time on beat-to-beat basis. Insofar as real-time tracking is concerned, in at least some cases, beat-to-beat changes in LAP are correlated with beat-to-beat changes in cardiogenic fractionation. For example, atrial fibrillation (AF) may induce both an increase in LAP and an increase in fractionation of the cardiogenic impedance waveform. In some implementations, it is desirable to trigger the estimation of LAP based on changes in cardiac rhythm. For example, the detection of a sharp increase in atrial rate may be used to activate the LAP estimation system to estimate LAP.

Figure 17:
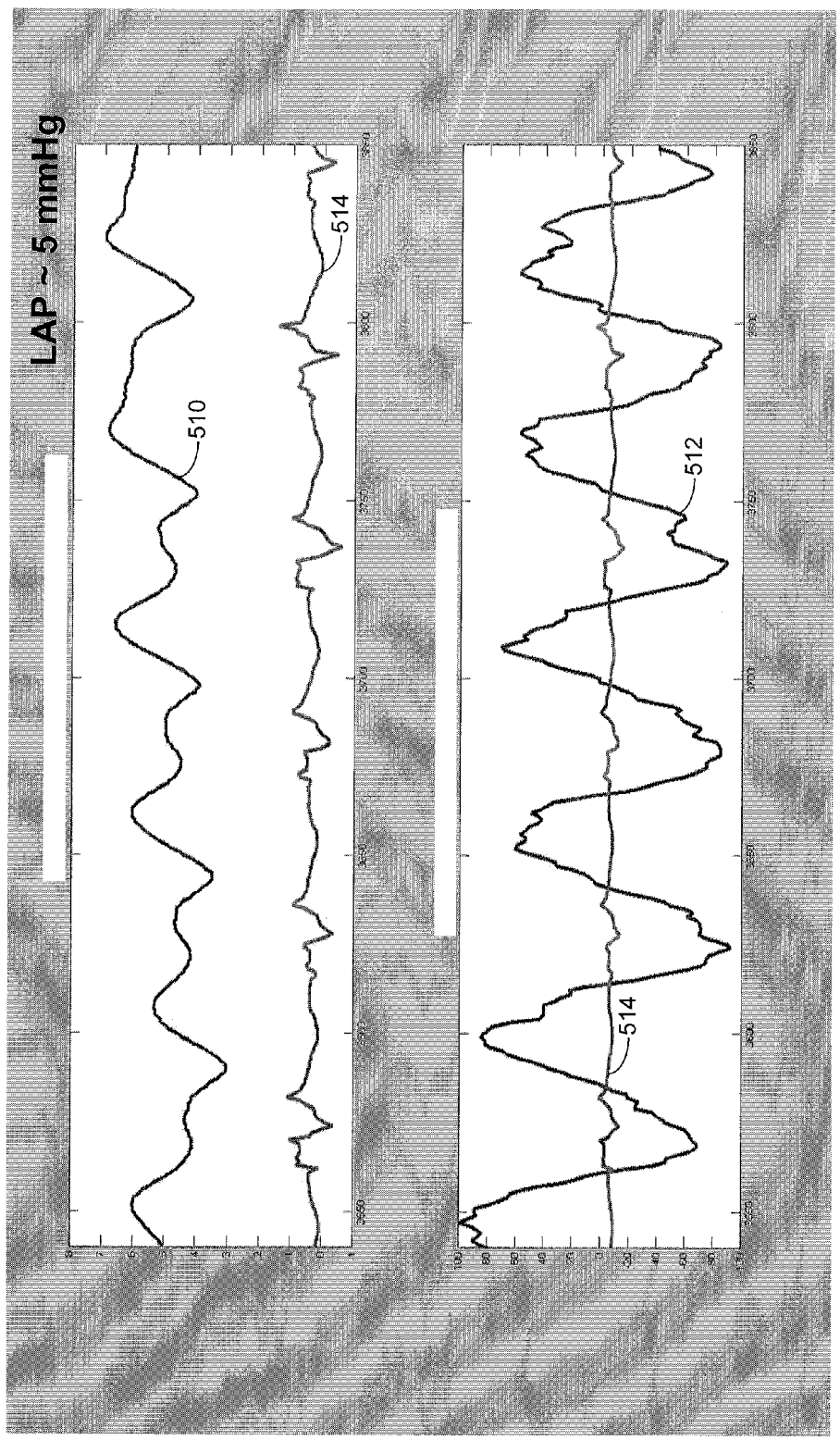
FIG. 17 is another graph illustrating exemplary cardiogenic impedance signals that may be processed in accordance with the technique of FIG. 15, and particularly illustrating the lack of fractionation of the cardiogenic impedance signal exhibited without heart failure in an animal test subject.
Figure 18:
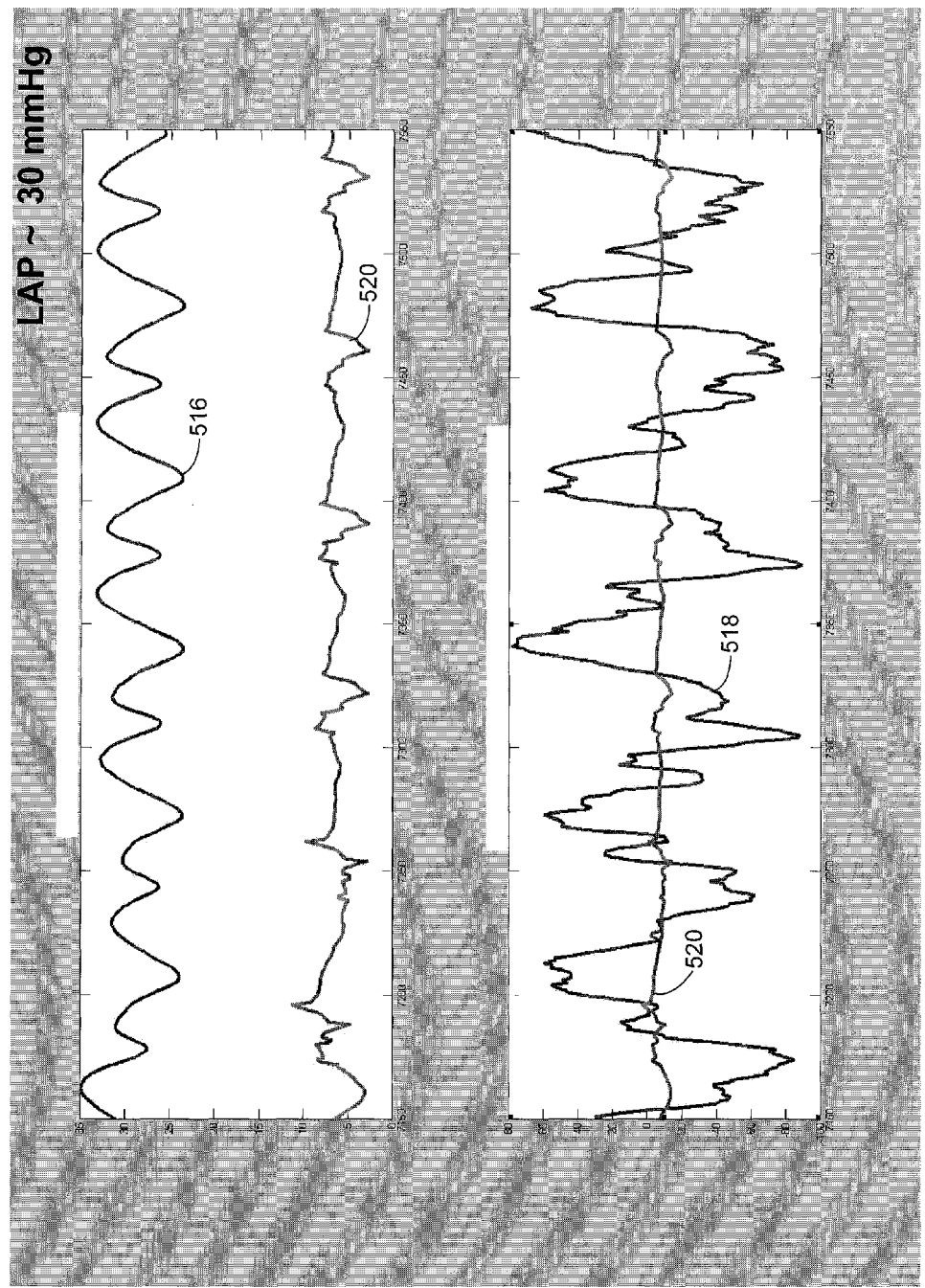
FIG. 18 is another graph illustrating exemplary cardiogenic impedance signals that may be processed in accordance with the technique of FIG. 15, and particularly illustrating elevated LAP levels and corresponding fractionation of a cardiogenic impedance signal exhibited during heart failure as emulated in an animal test subject.

FIGS. 17 and 18 provide additional graphs illustrating fractionation. FIG. 17 illustrates a data obtained from an animal test subject with healthy heart. An LAP trace 510 exhibits nominal pressure levels of about 5 mmHg. The corresponding cardiogenic impedance trace 512 exhibits very little fractionation. An IEGM 514 is also illustrates in each graph (subject to differing vertical scales.) The time scale for the figure covers only a few heartbeats. Heart failure was then emulated in this test subject and additional LAP and cardiogenic impedance traces were obtained, which are shown in FIG. 18. More specifically, FIG. 18 illustrates data obtained from the same test subject two hours later after heart failure was emulated. An LAP trace 516 exhibits elevated pressure levels of about 30 mmHg. The corresponding cardiogenic impedance trace 518 exhibits substantial fractionation. An IEGM 520 is also illustrates in each graph (again subject to differing vertical scales.) As before, the time scale for the figure covers only a few heartbeats. As can be seen from a comparison of the two graphs, the elevated LAP associated with heart failure correlates with increased fractionation.

Thus, a variety of techniques for estimating LAP and tracking heart failure are provided. These may be supplemented by using other non-impedance-based cardiac pressure detection and heart failure detection techniques. In some implementations, before an alarm is activated or any therapy is automatically delivered, the pacer/ICD employs at least one other detection technique to corroborate the detection of heart failure. Techniques for detecting or tracking heart failure are set forth the following patents and patent applications: U.S. Pat. No. 6,328,699 to Eigler, et al., entitled "Permanently Implantable System and Method for Detecting, Diagnosing and Treating Congestive Heart Failure"; U.S. Pat. No. 6,970,742 to Mann, et al., entitle "Method for Detecting, Diagnosing, and Treating Cardiovascular Disease"; U.S. Pat. No. 7,115,095 to Eigler, et al., entitled "Systems and Methods for Detecting, Diagnosing and Treating Congestive Heart Failure"; U.S. patent application Ser. No. 11/100,008, of Kil et al., entitled "System And Method For Detecting Heart Failure And Pulmonary Edema Based On Ventricular End-Diastolic Pressure Using An Implantable Medical Device", filed Apr. 5, 2005; U.S. patent application Ser. No. 11/014,276, of Min et al., entitled "System And Method For Predicting Heart Failure Based On Ventricular End-Diastolic Volume/Pressure Using An Implantable Medical Device", filed Dec. 15, 2004; U.S. patent application Ser. No. 10/810,437, of Bornzin et al., entitled "System and Method for Evaluating Heart Failure Based on Ventricular End-Diastolic Volume Using an Implantable Medical Device," filed Mar. 26, 2004 and U.S. patent application Ser. No. 10/346,809, of Min et al., entitled "System and Method for Monitoring Cardiac Function via Cardiac Sounds Using an Implantable Cardiac Stimulation Device," filed Jan. 17, 2003. See also: U.S. Pat. No. 6,572,557, to Tchou, et al., cited above. U.S. Pat. No. 6,645,153, to Kroll et al., entitled "System and Method for Evaluating Risk of Mortality Due To Congestive Heart Failure Using Physiologic Sensors", and U.S. Pat. No. 6,438,408 to Mulligan et al., entitled "Implantable Medical Device For Monitoring Congestive Heart Failure."

Also, other calibration procedures may potentially be exploited in connection with the calibration techniques described herein. See, for example, U.S. Patent Application 2004/0019285 of Eigler, et al., cited above, particularly the various linear regression techniques discussed therein.

Although primarily described with respected to examples having a pacer/ICD, other implantable medical devices may be equipped to exploit the techniques described herein. For the sake of completeness, an exemplary pacer/ICD will now be described, which includes components for performing the functions and steps already described. Also, an exemplary external programmer will be described, which includes components for performing the calibration steps already described.

Exemplary Pacer/ICD

Figure 20:
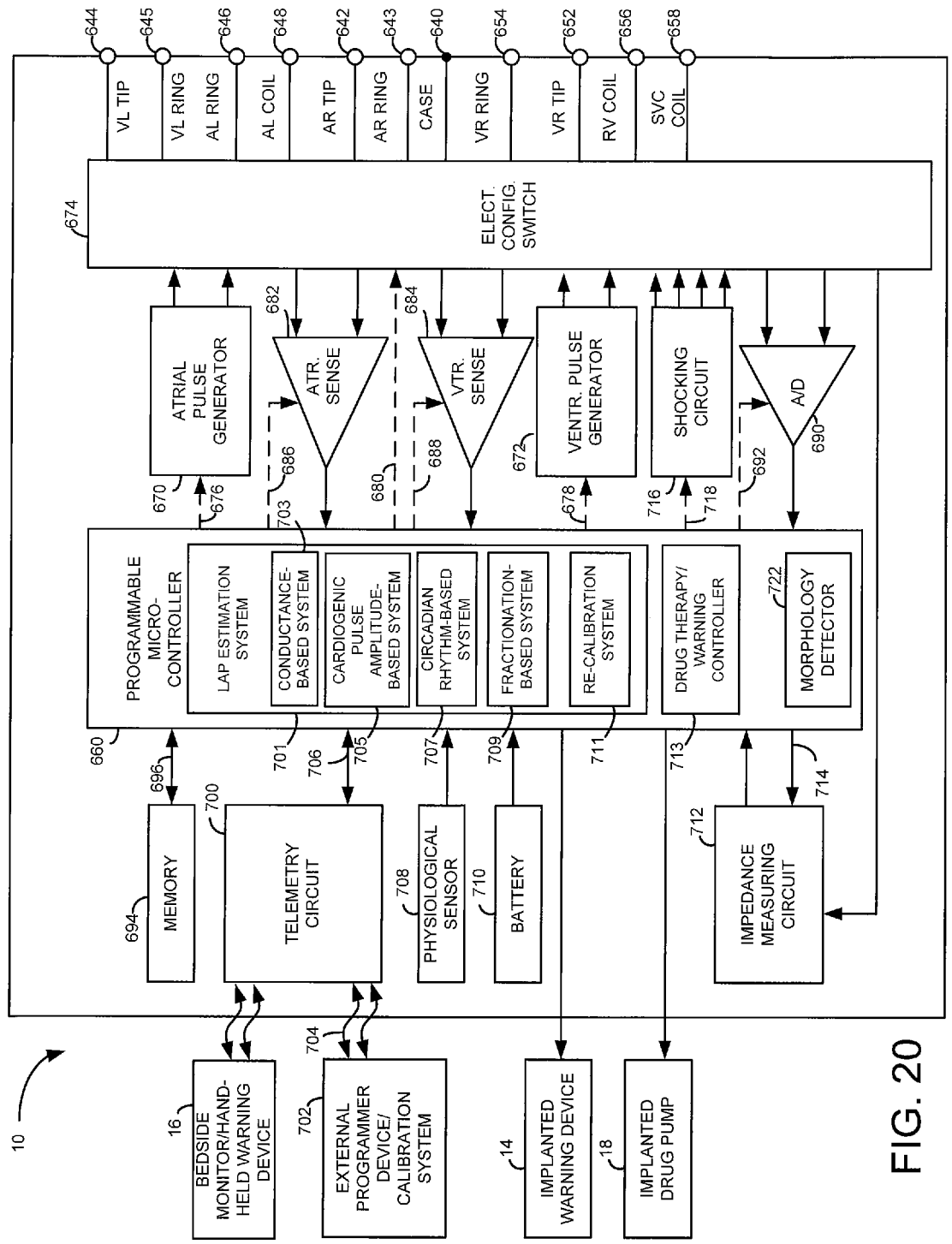
FIG. 20 a functional block diagram of the pacer/ICD of FIG. 19, illustrating basic circuit elements that provide cardioversion, defibrillation and/or pacing stimulation in the heart and particularly illustrating components for estimating LAP based on impedance.
Figure 21:
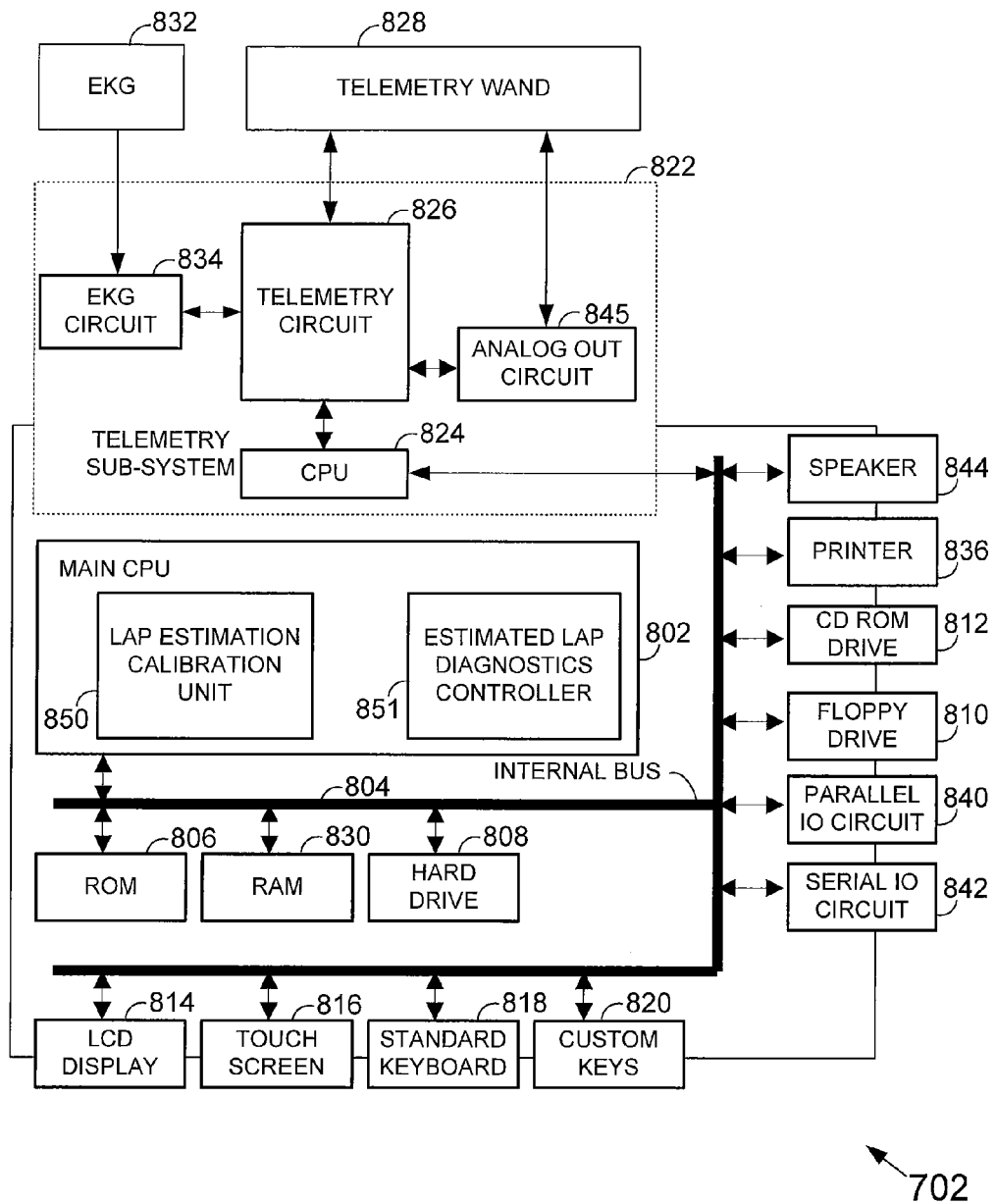
FIG. 21 is a functional block diagram illustrating components of a device programmer of FIG. 20, and in particular illustrating a programmer-based LAP estimation calibration system.

With reference to FIGS. 19 and 20, a description of an exemplary pacer/ICD will now be provided. FIG. 19 provides a simplified block diagram of the pacer/ICD, which is a dual-chamber stimulation device capable of treating both fast and slow arrhythmias with stimulation therapy, including cardioversion, defibrillation, and pacing stimulation, and also capable of estimating LAP or other forms of cardiac pressure using impedance signals. To provide other atrial chamber pacing stimulation and sensing, pacer/ICD 10 is shown in electrical communication with a heart 612 by way of a left atrial lead 620 having an atrial tip electrode 622 and an atrial ring electrode 623 implanted in the atrial appendage. Pacer/ICD 10 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a CS lead 624 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 624 is designed to receive atrial and ventricular cardiac signals and to deliver left ventricular pacing therapy using at least a left ventricular tip electrode 626 and a LV ring electrode 625, left atrial pacing therapy using at least a left atrial ring electrode 627, and shocking therapy using at least a left atrial coil electrode 628. With this configuration, biventricular pacing can be performed. Although only three leads are shown in FIG. 19, it should also be understood that additional leads (with one or more pacing, sensing and/or shocking electrodes) might be used and/or additional electrodes might be provided on the leads already shown.

A simplified block diagram of internal components of pacer/ICD 10 is shown in FIG. 20. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 640 for pacer/ICD 10, shown schematically in FIG. 20, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, 644, 645, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 623. To achieve left chamber sensing, pacing and shocking, the connector includes at least a left ventricular tip terminal ($V_L$ TIP) 644, a left ventricular ring terminal ($V_L$ RING) 645, a left atrial ring terminal ($A_L$ RING) 646, and a left atrial shocking terminal ($A_L$ COIL)

648, which are adapted for connection to the left ventricular ring electrode 626, the left atrial ring electrode 627, and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal ($V_R$ COIL) 656, and an SVC shocking terminal (SVC COIL) 658, which are adapted for connection to the right ventricular tip electrode 632, right ventricular ring electrode 634, the $V_R$ coil electrode 636, and the SVC coil electrode 638, respectively.

At the core of pacer/ICD 10 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 20, an atrial pulse generator 670 and a ventricular pulse generator 672 generate pacing stimulation pulses for delivery by the right atrial lead 620, the right ventricular lead 630, and/or the CS lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, CS lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, pacer/ICD 10 utilizes the atrial and ventricular sensing circuits, 682 and 684, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 690. The data acquisition system 690 is configured to acquire intracardiac electrogram signals, convert the raw analog data into a digital signal, and store the digital signals for later processing and/or telemetric transmission to an external device 702. The data acquisition system 690 is coupled to the right atrial lead 620, the CS lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 694 through a telemetry circuit 700 in telemetric communication with the external device 702, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of pacer/ICD 10 (as contained in the microcontroller 660 or memory 694) to be sent to the external device 702 through an established communication link 704. Pacer/ICD 10 further includes an accelerometer or other physiologic sensor 708, commonly referred to as a "rate-responsive" sensor because it is typically used to adjust pacing stimulation rate according to the exercise state of the patient. However, the physiological sensor 708 may further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV delay, V-V delay, etc.) at which the atrial and ventricular pulse generators, 670 and 672, generate stimulation pulses. While shown as being included within pacer/ICD 10, it is to be understood that the physiologic sensor 708 may also be external to pacer/ICD 10, yet still be implanted within or carried by the patient. A common type of rate responsive sensor is an activity sensor incorporating an accelerometer or a piezoelectric crystal, which is mounted within the housing 640 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 710, which provides operating power to all of the circuits shown in FIG. 6. The battery 710 may vary depending on the capabilities of pacer/ICD 10. If the system only provides low voltage therapy, a lithium iodine or lithium copper fluoride cell typically may be utilized. For pacer/ICD 10, which employs shocking therapy, the battery 710 should be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, appropriate batteries are employed.

As further shown in FIG. 20, pacer/ICD 10 is shown as having an impedance measuring circuit 712, which is enabled by the microcontroller 660 via a control signal 714. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 712 is advantageously coupled to the switch 774 so that any desired electrode may be used. The impedance measuring circuit 712 also detects the impedance signals discussed above to use in estimating LAP. That is, impedance measuring circuit 712 is an electrical impedance (Z) detector operative to detect an electrical impedance (Z) signal within the patient along at least one sensing vector wherein impedance is affected by cardiac pressure.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 joules), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

Insofar as LAP estimation is concerned, the microcontroller includes an LAP estimation system 701 operative to estimate LAP or other forms of cardiac pressure based on parameters derived from impedance signals using the techniques described above. That is estimation system is operative to: measure a predetermined parameter within patient tissues, the parameter being influenced by an electrical field applied to tissues of the patient including cardiac tissues, the parameter also being affected by cardiac pressure; and estimate cardiac pressure within the patient by applying predetermined conversion factors to the measured parameter. For example, the estimation system may be equipped to detect an electrical impedance (Z) signal within the patient along a sensing vector wherein impedance is affected by cardiac pressure; derive a predetermined parameter from the electrical impedance (Z) signal; input predetermined conversion factors from memory for converting the parameter derived from the electrical impedance signal (Z) to cardiac pressure; and estimate cardiac pressure within the patient by applying the conversion factors to the parameter derived from the electrical impedance (Z) signal. Estimation system 701 includes: a conductance-based system 703 operative to estimate cardiac pressure within the patient by applying the conversion factors to electrical conductance parameters derived from the electrical impedance (Z) signal; an cardiogenic pulse amplitude-based system 705 operative to estimate cardiac pressure within the patient by applying the conversion factors to cardiogenic pulse amplitude parameters derived from the electrical impedance (Z) signal; a circadian pulse amplitude-based system 707 operative to estimate cardiac pressure within the patient by applying the conversion factors to circadian pulse amplitude parameters derived from the electrical impedance (Z) signal; and a fractionation-based system 709 operative to estimate cardiac pressure within the patient by applying the conversion factors to cardiogenic impedance fractionation parameters derived from the electrical impedance (Z) signal. Estimation system 701 also includes a re-calibration unit 711 operative to re-calibrate the conversion factors using techniques described above.

Diagnostic data pertaining to LAP is stored in memory 694. Warning and/or notification signals are generated, when appropriate, by a warning controller 713 then relayed to the bedside monitor 18 via telemetry system 700 or to external programmer 702 (or other external calibration system.) Controller 713 can also controller an implantable drug pump, if one is provided, to deliver appropriate medications. Terminals for connecting the implanted warning device and the implanted drug pump to the pacer/ICD are not separately shown. Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

Exemplary External Programmer

FIG. 21 illustrates pertinent components of an external programmer 702 for use in programming the pacer/ICD of FIG. 20 and for performing the above-described calibration techniques. For the sake of completeness, other device programming functions are also described herein. Generally, the programmer permits a physician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 702 may also be capable of processing and analyzing data received from the implanted device and from the EKG leads to, for example, render preliminary diagnosis as to medical conditions of the patient or to the operations of the implanted device.

Now, considering the components of programmer 702, operations of the programmer are controlled by a CPU 802, which may be a generally programmable microprocessor or microcontroller or may be a dedicated processing device such as an application specific integrated circuit (ASIC) or the like. Software instructions to be performed by the CPU are accessed via an internal bus 804 from a read only memory (ROM) 806 and random access memory 830. Additional software may be accessed from a hard drive 808, floppy drive 810, and CD ROM drive 812, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 814 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 816 overlaid on the LCD display or through a standard keyboard 818 supplemented by additional custom keys 820, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 702 to retrieve data stored within any implanted devices and to also retrieve EKG data from EKG leads, if any, coupled to the patient. To this end, CPU 802 transmits appropriate signals to a telemetry subsystem 822, which provides components for directly interfacing with the implanted devices, and the EKG leads. Telemetry subsystem 822 includes its own separate CPU 824 for coordinating the operations of the telemetry subsystem. Main CPU 802 of programmer communicates with telemetry subsystem CPU 824 via internal bus 804. Telemetry subsystem additionally includes a telemetry circuit 826 connected to telemetry wand 828, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 834 for receiving surface EKG signals from a surface EKG system 832. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the pacer/ICD also includes the data stored within the recalibration database of the pacer/ICD (assuming the pacer/ICD is equipped to store that data.) Data retrieved from the implanted devices is stored by external programmer 702 either within a random access memory (RAM) 830, hard drive 808 or within a floppy diskette placed within floppy drive 810. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 702, the implanted devices may be further controlled to transmit additional data in real time as it is detected by the implanted devices, such as additional IEGM data, lead impedance data, and the like. Additionally, or in the alternative, telemetry subsystem 822 receives EKG signals from EKG leads 832 via an EKG processing circuit 834. As with data retrieved from the implanted device itself, signals received from the EKG leads are stored within one or more of the storage devices of the external programmer. Typically, EKG leads output analog electrical signals representative of the EKG. Accordingly, EKG circuit 834 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 802, the programming commands are converted to specific programmable parameters for transmission to the implanted devices via telemetry wand 828 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 836.

Additionally, CPU 802 also preferably includes an LAP estimation calibration unit 850 operative to perform the calibration procedures described above. CPU 802 also preferably includes an estimated LAP diagnostics controller 851 operative to control the display of estimated LAP values. As already noted, physician are often more familiar with LAP value than impedance values and hence benefit from LAP-based diagnostics displays that graphically illustrates changes in LAP within the patient, such as changes brought on by heart failure.

Programmer/monitor 702 also includes a modem 838 to permit direct transmission of data to other programmers via the public switched telephone network (PSTN) or other interconnection line, such as a T1 line or fiber optic cable. Depending upon the implementation, the modem may be connected directly to internal bus 804 may be connected to the internal bus via either a parallel port 840 or a serial port 842. Other peripheral devices may be connected to the external programmer via parallel port 840 or a serial port 842 as well. Although one of each is shown, a plurality of input output (IO) ports might be provided. A speaker 844 is included for providing audible tones to the user, such as a warning beep in the event improper input is provided by the physician. Telemetry subsystem 822 additionally includes an analog output circuit 845 for controlling the transmission of analog output signals, such as IEGM signals output to an EKG machine or chart recorder.

With the programmer configured as shown, a physician or other user operating the external programmer is capable of retrieving, processing and displaying a wide range of information received from the implanted devices and to reprogram the implanted device if needed. The descriptions provided herein with respect to FIG. 21 are intended merely to provide an overview of the operation of programmer and are not intended to describe in detail every feature of the hardware and software of the programmer and is not intended to provide an exhaustive list of the functions performed by the programmer.

Figure 22:
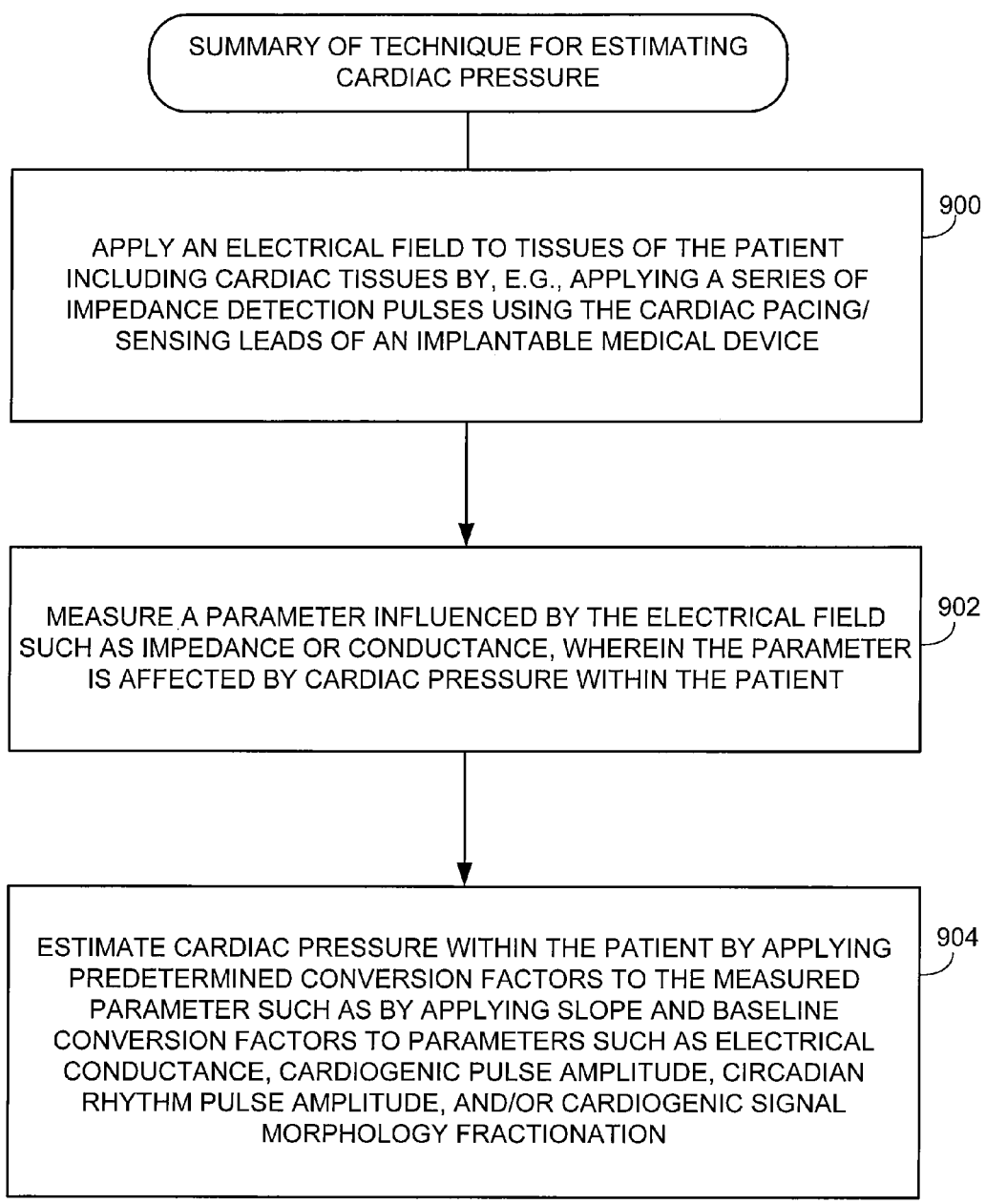
FIG. 22 is a flow diagram broadly summarizing the cardiac pressure estimation techniques that may be performed by the system of FIG. 1 or other implantable medical systems.

FIG. 22 provides a broad summary of the techniques discussed above. At step 900, an electrical field is applied to tissues of the patient, including cardiac tissues by, e.g., applying a series of impedance detection pulses using the cardiac pacing/sensing leads of an implantable medical device. Impedance detection pulses may be generated, for example, using the atrial or ventricular pulse generators of FIG. 20 and then applied to the tissues of the patient via the electrodes of FIG. 19. At step 902, a parameter is measured that is influenced by the electrical field, such as impedance or conductance, wherein the parameter is also affected by cardiac pressure within the patient. Impedance may be measured, for example, using the impedance measuring circuit of FIG. 20. At step 904, cardiac pressure is estimated within the patient by applying predetermined conversion factors to the measured parameter, such as by applying slope and baseline conversion factors to parameters such as electrical conductance, cardiogenic pulse amplitude, circadian rhythm pulse amplitude, and/or cardiogenic signal morphology fractionation, using techniques described above. Cardiac pressure may be estimated, for example, using the LAP estimation system of FIG. 20.

In general, while the invention has been described with reference to particular embodiments, modifications can be made thereto without departing from the spirit and scope of the invention. Note also that the term "including" as used herein is intended to be inclusive, i.e. "including but not limited to".

What is claimed is:

1. A method for estimating cardiac pressure within a patient using an implantable medical device, the method comprising:
    applying an electrical impedance detection pulse from which electrical impedance can be measured to tissues of the patient including cardiac tissues;
    measuring a parameter influenced by the electrical impedance detection pulse, the parameter being affected by cardiac pressure, the measuring comprising:
        detecting an electrical impedance (Z) signal within the patient along a sensing vector wherein impedance is affected by cardiac pressure; and
        deriving the parameter from the electrical impedance (Z) signal; and
    estimating, by a processor of the implantable medical device, cardiac pressure within the patient by applying predetermined conversion factors to the measured parameter by recalling predetermined conversion factors from a memory of the implantable medical device, wherein the predetermined conversion factors are configured to convert the parameter to cardiac pressure by inputting slope and baseline values representative of a linear relationship between cardiac pressure and the parameter.

2. The method of claim 1 wherein the predetermined parameter is a cardiogenic pulse amplitude value and wherein the conversion factors are cardiogenic pulse amplitude-based conversion factors for converting cardiogenic pulse amplitude values to cardiac pressure values.

3. The method of claim 2 wherein estimating cardiac pressure includes applying the cardiogenic pulse amplitude-based conversion factors to cardiogenic pulse amplitudes derived from an electrical impedance (Z) signal.

4. The method of claim 1 wherein the predetermined parameter is a circadian rhythm pulse amplitude value and wherein the conversion factors are circadian rhythm-based conversion factors for converting circadian rhythm pulse amplitude values to cardiac pressure values.

5. The method of claim 4 wherein estimating cardiac pressure includes applying the cardiogenic pulse amplitude-based conversion factors to cardiogenic pulse amplitudes derived from the electrical impedance (Z) signal.

6. The method of claim 1 wherein the predetermined parameter is a cardiogenic signal fractionation parameter and wherein the conversion factors are fractionation-based conversion factors for converting fractionation parameters to cardiac pressure values.

7. The method of claim 6 wherein estimating cardiac pressure includes applying the fractionation-based conversion factors to cardiogenic fractionation parameters derived from an electrical impedance (Z) signal.

8. The method of claim 6 wherein the fractionation parameter represents the fractionation of a cardiogenic component of the electrical impedance (Z) signal.

9. The method of claim 6 wherein the fractionation parameter represents the fractionation of a circadian component of the electrical impedance (Z) signal.

10. The method of claim 1 wherein the parameter includes one or more of: an electrical conductance (G) value, a cardiogenic pulse amplitude value, a circadian rhythm pulse amplitude, and a cardiogenic signal morphology fractionation parameter.

11. The method of claim 1 wherein the predetermined parameter is an electrical conductance (G) value and wherein the predetermined conversion factors are conductance-based conversion factors for converting electrical cardiac conductance (G) values to cardiac pressure values.

12. The method of claim 11 wherein electrical conductance (G) value is derived from the detected impedance (Z) by calculating the reciprocal of the detected impedance (Z).

13. The method of claim 11 wherein the predetermined conversion factors includes slope and baseline values representative of a linear relationship between conductance (G) and cardiac pressure; and
wherein estimating cardiac pressure includes applying the slope and baseline values to convert electrical conductance (G) values to cardiac pressure values.

14. The method of claim 13 wherein estimating cardiac pressure includes calculating:

Cardiac Pressure=$G$*Slope+Baseline.

15. The method of claim 13 wherein electrical conductance (G) value is derived from impedance values (Z) measured along a sensing vector through the left atrium of the heart of the patient and wherein the resulting cardiac pressure value is an estimated left atrial pressure (eLAP) value obtained by calculating:

eLAP=$G$*Slope+bLAP;

wherein Slope is a slope value specifically for use with left atrial pressure (LAP) and bLAP is a baseline value specifically for use with LAP.

16. The method of claim 13 further including an initial calibration step for determining the slope and baseline values that are representative of the linear relationship between conductance (G) and cardiac pressure for the particular patient.

17. The method of claim 16 wherein determining the slope and baseline values includes:
transmitting, to an external calibration system, a first conductance calibration value ($G_1$) detected by an implantable medical device and a corresponding first cardiac pressure calibration value ($Pressure_1$) measured by a device other than the implantable medical device at a first time within the patient; and
inputting, to the external calibration system, a second conductance calibration value ($G_2$) detected by the implantable medical device and a corresponding second cardiac pressure calibration value ($Pressure_2$) measured by a device other than the implantable medical device at a second time within the patient, wherein the first and second cardiac pressure values ($Pressure_1$, $Pressure_2$) differ substantially.

18. The method of claim 17 wherein determining the slope is performed by calculating:

Slope=($Pressure_2$−$Pressure_1$)/($G_2$−$G_1$).

19. The method of claim 18 wherein determining the baseline is performed by calculating:

Baseline=$Pressure_2$−Slope*$G_1$.

20. The method of claim 17 wherein the first and second conductance calibration values ($G_1$, $G_2$) are derived from first and second impedance calibration values ($Z_1$, $Z_2$), respectively, measured within the patient at times when the first and second cardiac pressure values ($Pressure_1$, $Pressure_2$), respectively, are measured.

21. The method of claim 20 further including additional calibration steps of:
detecting the first cardiac pressure value ($Pressure_1$) and the first conductance calibration value ($G_1$) while the patient is at rest; and
detecting the second cardiac pressure value ($Pressure_2$) and the second conductance calibration value ($G_2$) while the patient is subject to a condition significantly affecting cardiac pressure within the patient, wherein detecting the first and second conductance calibration values ($G_1$, $G_2$) are measured within the patient using the implantable medical device and detecting the first and second cardiac pressure values ($Pressure_1$, $Pressure_2$) are measured within the patient using a Swan-Ganz catheter equipped to measure pulmonary capillary wedge pressure (PCWP).

22. The method of claim 21 wherein the condition significantly affecting cardiac pressure within the patient includes one or more of: isometric muscle contraction, vasodilatation, vasoconstriction, rapid pacing and performance of the Valsalva maneuver.

23. The method of claim 20 wherein the cardiac pressure value to be estimated is an effective pressure value and wherein the method further includes additional calibration steps of:
detecting the first cardiac pressure value ($Pressure_1$) using a Swan-Ganz catheter equipped to measure pulmonary capillary wedge pressure (PCWP) and the first impedance calibration value ($Z_1$) within the patient at a time of device implant; and
detecting an additional impedance calibration value ($Z_N$) during performance of a Valsalva maneuver by the patient at a time subsequent to implant, wherein detecting the first and second impedance calibration values ($Z_1$, $Z_N$) are measured within the patient using the implantable medical device.

24. The method of claim 23 wherein following device implant, only the baseline value is recalibrated based on an additional conductance value ($G_N$) derived from the additional impedance value ($Z_N$):

Baseline=−Slope*$G_N$.

25. The method of claim 23 wherein following device implant the slope and baseline values are re-calibrated based on an additional conductance value ($G_N$) derived from the additional impedance value ($Z_N$) and on a first effective cardiac pressure value ($Pressure_1$):

$Slope_G$=−$LAP_1$/($G_N$−$G_1$) and $Baseline_G$=−New_$Slope_G$*$G_N$, where $Slope_G$ is a articular sloe value $LAP_1$ is a first cardiac pressure calibration value, $Baseline_G$ is a articular baseline value, and New $Slope_G$ is a new sloe value.

26. The method of claim 23 wherein the effective cardiac pressure value might not drop to zero within the patient during Valsalva and wherein an additional correction factor is calculated at device implant.

27. The method of claim 13 further including an initial calibration step of determining the slope and baseline values that are representative of the linear relationship between conductance (G) and cardiac pressure for any of a plurality of patients.

28. The method of claim 26 wherein determining the slope and baseline values includes:
transmitting, to an external calibration system, a plurality of conductance values (G) detected by the internal medical device and corresponding cardiac pressure values (Pressure) measured by a device other than the implantable medical device within a plurality of test subjects; and determining, by the external calibration system, slope and baseline values by applying linear regression to the plurality of conductance values (G) and cardiac pressure values (Pressure) obtained from the test subjects.

29. The method of claim 27 wherein the conductance values (G) are derived by the external calibration system from impedance values (Z) measured by implantable medical devices along sensing vectors passing through the left atria of the hearts of each of the test subjects and wherein the cardiac pressure values obtained by temporary pressure sensors inserted within each of the test subjects.

30. The method of claim 1 further including controlling therapy based on estimated cardiac pressure.

31. The method of claim 30 wherein the implantable device is equipped with an implantable drug pump and wherein drug therapy is controlled based on estimated cardiac pressure.

32. The method of claim 1 further including detecting heart failure based on estimated cardiac pressure.

33. The method of claim 32 wherein the implantable device is equipped with an implantable warning device and wherein a warning is generated upon detection of heart failure.

34. The method of claim 32 wherein the implantable device is equipped to transmit signals to an external display device and wherein the warning is transmitted to the external device.

35. The method of claim 1 wherein the implantable device is equipped to transmit signals to an external display device and wherein estimated cardiac pressure values are transmitted to the external device.

36. A system for estimating cardiac pressure within a patient using an implantable medical device, the system comprising:

means for applying an electrical field to tissues of the patient including cardiac tissues;

means for measuring an electrical conductance (G) value, the electrical conductance (G) value being affected by cardiac pressure; and means for estimating cardiac pressure within the patient by applying slope and baseline values representative of a linear relationship between the electrical conductance (G) value and cardiac pressure to convert electrical conductance (G) values into cardiac pressure values according to the relationship:

$$\text{Cardiac Pressure} = G * \text{Slope} + \text{Baseline}.$$

37. The system of claim 36 wherein the electrical conductance (G) value is derived from impedance values (Z) measured along a sensing vector through the left atrium of the heart of the patient and wherein the resulting cardiac pressure value is an estimated left atrial pressure (eLAP) value obtained by calculating:

$$eLAP = G * \text{Slope} + bLAP;$$

wherein Slope is a slope value specifically for use with left atrial pressure (LAP) and bLAP is a baseline value specifically for use with LAP.

38. The system of claim 36 further including an initial calibration means for determining the slope and baseline values that are representative of the linear relationship between electrical conductance (G) value and cardiac pressure for the particular patient.

39. The system of claim 37 wherein the initial calibration means comprises:

means for transmitting, to an external calibration system, a first conductance calibration value ($G_1$) detected by an implantable medical device and a corresponding first cardiac pressure calibration value ($\text{Pressure}_1$) measured by a device other than the implantable medical device at a first time within the patient; and means for inputting, to the external calibration system, a second conductance calibration value ($G_2$) detected by the implantable medical device and a corresponding second cardiac pressure calibration value ($\text{Pressure}_2$) measured by a device other than the implantable medical device at a second time within the patient, wherein the first and second cardiac pressure values ($\text{Pressure}_1$, $\text{Pressure}_2$) differ substantially.

40. The system of claim 39 wherein determining the slope is performed by calculating:

$$\text{Slope} = (\text{Pressure}_2 - \text{Pressure}_1)/(G_2 - G_1); \text{ and}$$

determining the baseline is performed by calculating:

$$\text{Baseline} = \text{Pressure}_2 - \text{Slope} * G_1.$$

41. The system of claim 39 wherein the first and second conductance calibration values ($G_1$, $G_2$) are derived from first and second impedance calibration values ($Z_1$, $Z_2$), respectively, measured within the patient at times when the first and second cardiac pressure values ($\text{Pressure}_1$, $\text{Pressure}_2$), respectively, are measured.

42. The system of claim 36 further comprising an initial calibration means for determining the slope and baseline values that are representative of the linear relationship between electrical conductance (G) values and cardiac pressures for any of a plurality of patients.

43. A method for estimating cardiac pressure within a patient using an implantable medical device, the method comprising:

applying an electrical field to tissues of the patient including cardiac tissues;

measuring an electrical conductance (G) value, the electrical conductance (G) value being affected by cardiac pressure; and estimating, by a processor of the implantable medical device, cardiac pressure within the patient by applying slope and baseline values representative of a linear relationship between the electrical conductance (G) value and cardiac pressure to convert electrical conductance (G) values into cardiac pressure values according to the relationship:

$$\text{Cardiac Pressure} = G * \text{Slope} + \text{Baseline}.$$

44. The method of claim 43 further including controlling therapy based on estimated cardiac pressure.

45. The method of claim 44 wherein the implantable device is equipped with an implantable drug pump and wherein drug therapy is controlled based on estimated cardiac pressure.

46. The method of claim 43 further including detecting heart failure based on estimated cardiac pressure.

47. The method of claim 46 wherein the implantable device is equipped with an implantable warning device and wherein a warning is generated upon detection of heart failure.

48. The method of claim 46 wherein the implantable device is equipped to transmit signals to an external display device and wherein a warning is transmitted to the external device.

49. The method of claim 43 wherein the implantable device is equipped to transmit signals to an external display device and wherein estimated cardiac pressure values are transmitted to the external display device.

50. A method for estimating cardiac pressure within a patient using an implantable medical device, the method comprising:
- applying an electrical field to tissues of the patient including cardiac tissues;
- measuring a parameter influenced by the electrical field, the parameter being affected by cardiac pressure, wherein the parameter is an electrical conductance (G) value; and
- estimating, by a processor of the implantable medical device, cardiac pressure within the patient by applying predetermined conversion factors to the measured parameter, wherein the predetermined conversion factors are conductance-based conversion factors for converting electrical cardiac conductance (G) values to cardiac pressure values, the predetermined conversion factors include slope and baseline values representative of a linear relationship between conductance (G) and cardiac pressure, wherein the estimating further comprises:
  - applying the slope and baseline values to convert electrical conductance (G) values to cardiac pressure values; and
  - calculating:

Cardiac Pressure=G*Slope+Baseline.

51. The method of claim 50 further including an initial calibration step for determining the slope and baseline values that are representative of the linear relationship between electrical cardiac conductance (G) values and cardiac pressure for the particular patient.

52. The method of claim 51 wherein determining the slope and baseline values includes:
- transmitting, to an external calibration system, a first conductance calibration value ($G_1$) detected by an implantable medical device and a corresponding first cardiac pressure calibration value ($Pressure_1$) measured by a device other than the implantable medical device at a first time within the patient; and
- inputting, to the external calibration system, a second conductance calibration value ($G_2$) detected by the implantable medical device and a corresponding second cardiac pressure calibration value ($Pressure_2$) measured by a device other than the implantable medical device at a second time within the patient, wherein the first and second cardiac pressure values ($Pressure_1$, $Pressure_2$) differ substantially.

53. The method of claim 52 wherein the first and second conductance calibration values ($G_1$, $G_2$) are derived from first and second impedance calibration values ($Z_1$, $Z_2$), respectively, measured within the patient at times when the first and second cardiac pressure values ($Pressure_1$, $Pressure_2$), respectively, are measured.

54. The method of claim 53 further including additional calibration steps of:
- detecting the first cardiac pressure value ($Pressure_1$) and the first conductance calibration value ($G_1$) while the patient is at rest; and
- detecting the second cardiac pressure value ($Pressure_2$) and the second conductance calibration value ($G_2$) while the patient is subject to a condition significantly affecting cardiac pressure within the patient, wherein detecting the first and second conductance calibration values ($G_1$, $G_2$) are measured within the patient using the implantable medical device and detecting the first and second cardiac pressure values ($Pressure_1$, $Pressure_2$) are measured within the patient using a Swan-Ganz catheter equipped to measure pulmonary capillary wedge pressure (PCWP).

55. The method of claim 53 wherein the cardiac pressure value to be estimated is an effective pressure value and wherein the method further includes additional calibration steps of:
- detecting the first cardiac pressure value ($Pressure_1$) using a Swan-Ganz catheter equipped to measure pulmonary capillary wedge pressure (PCWP) and the first impedance calibration value ($Z_1$) within the patient at a time of device implant; and
- detecting an additional impedance calibration value ($Z_N$) during performance of a Valsalva maneuver by the patient at a time subsequent to implant, wherein detecting the first and second impedance calibration values ($Z_1$, $Z_N$) are measured within the patient using the implantable medical device.

56. The method of claim 55 wherein the effective cardiac pressure value might not drop to zero within the patient during Valsalva and wherein an additional correction factor is calculated at device implant.

57. The method of claim 56 wherein determining the slope and she baseline values includes:
- transmitting, to an external calibration system, a plurality of conductance values (G) detected by the internal medical device and corresponding cardiac pressure values (Pressure) measured by a device other than the implantable medical device within a plurality of test subjects; and
- determining, by the external calibration system, slope and baseline values by applying linear regression to the plurality of conductance values (G) and cardiac pressure values (Pressure) obtained from the test subjects.

58. The method of claim 50 further including an initial calibration step of determining the slope and baseline values that are representative of the linear relationship between electrical cardiac conductance (G) values and cardiac pressure for any of a plurality of patients.

59. The method of claim 58 wherein the conductance values (G) are derived by an external calibration system from impedance values (Z) measured by the implantable medical device along sensing vectors passing through a left atria of the hearts of each of the plurality of patients and wherein the cardiac pressure values obtained by temporary pressure sensors inserted within each of the plurality of patients subjects.

60. The method of claim 50 wherein the electrical cardiac conductance (G) value is derived from a detected impedance (Z) value by calculating the reciprocal of the detected impedance (Z) value.

* * * * *